US008318187B2

(12) United States Patent
Sabino et al.

(10) Patent No.: US 8,318,187 B2
(45) Date of Patent: *Nov. 27, 2012

(54) LONG-WEARING COSMETIC COMPOSITIONS WITH IMPROVED SHINE

(75) Inventors: Michael Christopher Sabino, Cockeysville, MD (US); Marilyn Ann Glen, Baltimore, MD (US); Thomas Elliot Rabe, Baltimore, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 1951 days.

This patent is subject to a terminal disclaimer.

(21) Appl. No.: 11/116,879

(22) Filed: Apr. 28, 2005

(65) Prior Publication Data

US 2005/0244355 A1  Nov. 3, 2005

Related U.S. Application Data

(60) Provisional application No. 60/567,262, filed on Apr. 30, 2004.

(51) Int. Cl.
*A61Q 1/04* (2006.01)
*A61Q 1/06* (2006.01)

(52) U.S. Cl. .......................................... 424/401; 424/64

(58) Field of Classification Search ........................ None
See application file for complete search history.

(56) References Cited

U.S. PATENT DOCUMENTS

| | | | |
|---|---|---|---|
| 4,897,261 A | 1/1990 | Yamazaki et al. | |
| 5,120,529 A | 6/1992 | Koch et al. | |
| 5,538,717 A | 7/1996 | La Poterie | |
| 5,817,304 A | 10/1998 | Mondet et al. | |
| 5,849,275 A | 12/1998 | Calello et al. | |
| 5,925,337 A | 7/1999 | Arraudeau et al. | |
| 5,932,197 A | 8/1999 | Arnaud | |
| 5,972,354 A | 10/1999 | De La Poterie et al. | |
| 6,001,367 A | 12/1999 | Bazin et al. | |
| 6,010,686 A | 1/2000 | De La Poterie et al. | |
| 6,019,962 A | 2/2000 | Rabe et al. | |
| 6,024,946 A | 2/2000 | Dubief et al. | |
| 6,033,650 A | 3/2000 | Calello et al. | |
| 6,080,413 A | 6/2000 | Ellingson et al. | |
| 6,083,494 A | 7/2000 | Samain et al. | |
| 6,113,930 A | 9/2000 | Mondet et al. | |
| 6,123,931 A | 9/2000 | Ellingson et al. | |
| 6,126,929 A | 10/2000 | Mougin | |
| 6,143,283 A | 11/2000 | Calello et al. | |
| 6,180,122 B1 | 1/2001 | Roulier et al. | |
| 6,235,293 B1 | 5/2001 | De La Poterie et al. | |
| 6,238,654 B1 | 5/2001 | Tournilhac et al. | |
| 6,238,679 B1 | 5/2001 | De La Poterie | |
| 6,264,933 B1 | 7/2001 | Bodelin et al. | |
| 6,267,950 B1 | 7/2001 | De La Poterie et al. | |
| 6,280,750 B1 | 8/2001 | Roulier et al. | |
| 6,287,552 B1 | 9/2001 | Tournilhac et al. | |
| 6,294,158 B1 | 9/2001 | Dupuis | |
| 6,296,858 B1 | 10/2001 | Agostini et al. | |
| 6,306,411 B1 | 10/2001 | Jager Lezer | |
| 6,312,702 B2 | 11/2001 | Roulier et al. | |
| 6,342,237 B1 | 1/2002 | Bara | |
| 6,375,941 B1 | 4/2002 | Piot et al. | |
| 6,395,263 B1 | 5/2002 | Nichols et al. | |
| 6,413,526 B1 | 7/2002 | Bazin et al. | |
| 6,423,306 B2 | 7/2002 | Caes et al. | |
| 6,464,969 B2 | 10/2002 | De La Poterie et al. | |
| 6,482,398 B1 | 11/2002 | Rabe et al. | |
| 6,482,400 B1 | 11/2002 | Collin | |
| 6,485,731 B2 | 11/2002 | Calello et al. | |
| 6,491,931 B1 | 12/2002 | Collin | |
| 6,497,891 B2 | 12/2002 | Bara | |
| 6,503,495 B1 | 1/2003 | Alwattari et al. | |
| 6,509,009 B2 | 1/2003 | Nichols et al. | |
| 6,517,823 B1 | 2/2003 | Norman et al. | |
| 6,528,073 B2 | 3/2003 | Roulier et al. | |
| 6,555,097 B1 | 4/2003 | Rabe et al. | |
| 6,565,839 B2 | 5/2003 | De La Poterie et al. | |
| 6,641,823 B2 | 11/2003 | Piot et al. | |
| 6,656,483 B1 | 12/2003 | Farer et al. | |
| 6,811,770 B2 | 11/2004 | Ferrari et al. | |
| 6,958,155 B2 * | 10/2005 | Lu et al. ........................ 424/401 |
| 2001/0006653 A1 | 7/2001 | Roulier et al. | |
| 2001/0006665 A1 | 7/2001 | Auguste | |

(Continued)

FOREIGN PATENT DOCUMENTS

| | | |
|---|---|---|
| EP | 0705594 A1 | 12/1996 |
| EP | 0820764 A1 | 1/1998 |
| EP | 0875234 A1 | 11/1998 |
| EP | 0979642 A1 | 2/2000 |
| EP | 0847753 B1 | 5/2001 |
| JP | 09 315926 | 12/1997 |

(Continued)

*Primary Examiner* — Jyothsna Venkat
(74) *Attorney, Agent, or Firm* — Kenya T. Pierre; John G. Powell

(57) ABSTRACT

A cosmetic composition comprising (A) a first structured and adhesive film-forming fatty phase comprising (i) one or more lipidic components that are mutually compatible with one another when liquefied; (ii) at least one adhesive film-forming agent; and (iii) at least one lipophilic structuring agent in an amount effective to retain a second fatty phase entrapped in said cosmetic composition prior to application on mammalian keratinous tissue; and (B) a second fatty phase comprising at least one non-volatile lipidic component wherein said second fatty phase (B) is incompatible with said first structured and adhesive film-forming fatty phase (A) and said second fatty phase (B) is entrapped in said composition where upon application of said composition to mammalian keratinous tissue, said second fatty phase (B) readily separates from said composition to form a barrier layer over said first structured and adhesive film-forming fatty phase (A) and wherein said composition is substantially free of surfactants such that separation of said second fatty phase (B) from said composition is not prevented following application of said composition.

8 Claims, No Drawings

U.S. PATENT DOCUMENTS

| | | |
|---|---|---|
| 2001/0007654 A1 | 7/2001 | Caes et al. |
| 2001/0014313 A1 | 8/2001 | Roulier et al. |
| 2001/0031269 A1 | 10/2001 | Arnaud |
| 2001/0033846 A1 | 10/2001 | Roulier et al. |
| 2001/0055580 A1 | 12/2001 | Belli et al. |
| 2002/0015683 A1 | 2/2002 | Nichols et al. |
| 2002/0022009 A1 | 2/2002 | De La Poterie et al. |
| 2002/0035182 A1 | 3/2002 | L'Alloret et al. |
| 2002/0041857 A1 | 4/2002 | De La Poterie et al. |
| 2002/0044917 A1 | 4/2002 | De La Poterie et al. |
| 2002/0051759 A1 | 5/2002 | De La Poterie et al. |
| 2002/0058054 A1 | 5/2002 | Arnaud |
| 2002/0061319 A1 | 5/2002 | Bernard et al. |
| 2002/0061321 A1 | 5/2002 | Bara |
| 2002/0085986 A1 | 7/2002 | De La Poterie et al. |
| 2002/0098215 A1 | 7/2002 | Douin et al. |
| 2002/0098217 A1 | 7/2002 | Piot et al. |
| 2002/0102283 A1 | 8/2002 | Piot et al. |
| 2002/0110573 A1 | 8/2002 | Caes et al. |
| 2002/0159960 A1 | 10/2002 | Scancarella et al. |
| 2002/0168335 A1 | 11/2002 | Collin |
| 2002/0189030 A1 | 12/2002 | Collin |
| 2002/0192251 A1 | 12/2002 | Collin |
| 2003/0003154 A1 | 1/2003 | De La Poterie |
| 2003/0007944 A1 | 1/2003 | O'Halloran et al. |
| 2003/0012764 A1 | 1/2003 | Collin |
| 2003/0031640 A9 | 2/2003 | De La Poterie et al. |
| 2003/0039621 A1* | 2/2003 | Arnaud et al. ............... 424/63 |
| 2003/0064086 A1 | 4/2003 | Carrion et al. |
| 2003/0068344 A1 | 4/2003 | Ferrari et al. |
| 2003/0086887 A1 | 5/2003 | De La Poterie et al. |
| 2003/0086951 A9 | 5/2003 | Piot et al. |
| 2003/0103918 A1 | 6/2003 | Jose et al. |
| 2003/0118542 A1 | 6/2003 | Auguste et al. |
| 2003/0143171 A1 | 7/2003 | Nichols et al. |
| 2004/0022752 A1 | 2/2004 | De La Poterie |
| 2004/0126345 A1 | 7/2004 | McNamara |
| 2004/0126346 A1 | 7/2004 | Martin et al. |
| 2004/0180021 A1 | 9/2004 | De La Poterie |
| 2004/0228890 A1* | 11/2004 | Blin et al. ............... 424/401 |
| 2004/0234473 A1 | 11/2004 | Ferrari et al. |
| 2004/0265251 A1 | 12/2004 | Lee et al. |
| 2005/0031561 A1* | 2/2005 | Patil et al. ............... 424/63 |
| 2005/0065253 A1 | 3/2005 | Collin et al. |
| 2005/0095213 A1 | 5/2005 | Blin et al. |
| 2005/0129641 A1 | 6/2005 | Arnaud et al. |
| 2005/0175563 A1 | 8/2005 | McNamara et al. |
| 2005/0244442 A1 | 11/2005 | Sabino et al. |
| 2007/0154440 A1* | 7/2007 | Fleissman et al. ........ 424/70.122 |
| 2007/0166257 A1* | 7/2007 | Atis ............... 424/70.7 |

FOREIGN PATENT DOCUMENTS

| | | |
|---|---|---|
| WO | WO 96/14049 | 5/1996 |
| WO | WO 02/17864 A1 | 3/2002 |
| WO | WO 02/47619 A2 | 6/2002 |
| WO | WO 03/105789 * | 6/2003 |
| WO | WO 2004/108108 A1 | 12/2004 |

* cited by examiner

LONG-WEARING COSMETIC COMPOSITIONS WITH IMPROVED SHINE

CROSS REFERENCE TO RELATED APPLICATIONS

This application claims the benefit of U.S. Provisional application Ser. No. 60/567,262, filed on Apr. 30, 2004.

FIELD OF THE INVENTION

The present invention relates to long-wearing cosmetic compositions with improved gloss suitable for application to mammalian keratinous tissue including the skin, lips, eyelashes, eyebrows and nails comprising a first structured and adhesive film-forming fatty phase and a second fatty phase, wherein the second fatty phase is incompatible with the first structured and adhesive film-forming fatty phase and the second fatty phase is entrapped in the composition where upon application of the composition to mammalian keratinous tissue, the second fatty phase readily separates from the composition to form a barrier layer over the first structured and adhesive film-forming fatty phase and wherein the composition is substantially free of surfactants such that separation of the second fatty phase from the composition is not prevented following application of the composition.

BACKGROUND OF THE INVENTION

Cosmetic and other personal care products intended for use on human skin (such as foundation, concealer, eyeshadow, sunscreen and/or tanning products), lips (such as lipstick, lipcolor, lipliner, and lipgloss), and hair (such as mascara) often contain at least one fatty phase comprised of one or more substances that are oily, fatty, or waxy in nature. Depending on the intended product use, this fatty phase is primarily employed to deliver desirable features such as emolliency, spreadability, gloss, conditioning, and/or protective properties to the skin, lips, hair, or nails. Moreover, this fatty phase typically serves as a convenient and effective medium for dispersing and/or solubilizing other desirable ingredients into these compositions. Other desirable ingredients, for example, might include pigments, dyes, and/or particulate fillers to produce color or light scattering and/or reflecting effects desirable both in the product and on the skin, lips, hair and/or nails. These color and/or optical effects are typically desirable both in the product and on the skin, lips, hair and/or nails since they are capable of enhancing the visual attractiveness and appeal of the cosmetic product to the consumer. After product has been applied on the skin, lips, hair, and/or nails, these color and/or optical effects are highly desired for their ability to cover or reduce the appearance of fine lines/wrinkles or skin imperfections, and/or provide a more uniform skin tone, and/or provide color to accentuate the appearance of a consumer's face, lips, eyes, eyelashes, and/or nails. Additional desirable ingredients such as fragrance, vitamins, sunscreening agents, and other cosmetic or dermatological active agents might also be dispersed and/or solubilized into these compositions for their desired effects. Such products may be comprised of a fatty phase absent of water (typically referred to as anhydrous), or may be comprised of a fatty phase in combination with an aqueous phase to form a dispersion or emulsion of the water-in-oil (W/O) or oil-in-water (O/W) type. Such products take on various forms, such as solids or sticks, gels, pastes, creams, and lotions.

A common disadvantage often experienced by consumers using such products is the inability to sustain an initial or freshly applied look after application. Consumers would prefer to maintain the initial or freshly applied look for several hours or more (or at least experience minimal losses during such time) without the inconvenience of having to reapply product in order to restore or refresh the desired appearance. Unfortunately, the applied film of product very often remains too liquid-like or mobile, and therefore has the tendency to transfer easily from the skin, lips, and/or hair onto objects with which it is brought into contact, such as glassware, cups, fabrics, or other skin. Such contact with various objects is common and difficult to avoid in many daily activities, such as eating and drinking, as well as from inadvertent touching or rubbing of the skin, lips, and/or hair where a product film has been previously applied. Moreover, the mobility of the applied film often allows the product to migrate and/or concentrate easily into the fine lines, wrinkles, folds, and/or pores of the skin and/or lips, resulting in an undesirable non-uniform appearance.

In the case of anhydrous compositions (i.e., those lacking an aqueous phase), there have been a number of previous efforts disclosed that assertedly provide cosmetic products having long-lasting or transfer-resistant properties. Many of these efforts have relied on inclusion of high levels or proportions of volatile fatty phase liquid ingredients, such as volatile silicones or hydrocarbons, in the composition. Volatile fatty phase ingredients allow initial application or spreading but then evaporate from the product after application leaving a less mobile or more solid-like film. It has been common in such compositions to also depend on one or more hydrophobic resins, such as silicone resins, and/or high levels of one or more high melting point wax ingredients to deposit a rigid or solid-like film that is resistant to water. The resin and/or wax impart greater permanence and water-resistance to the applied film under such conditions as perspiration/sweating, washing, drinking, and swimming. However, the films obtained after application of these compositions and evaporation of the volatile fatty ingredients, typically have the disadvantage of being too dry in feel and/or appearance (i.e., very matte, not very glossy).

In the case of W/O and O/W dispersion or emulsion compositions, previous efforts also have been disclosed in the art that assertedly provide cosmetic products having long-lasting or transfer-resistant properties. Some of these efforts have been directed to the inclusion of water-soluble film-formers or gelling agents into the aqueous phase to deliver a harder or more rigid film following application. However, the films obtained after application of these compositions and evaporation of the water often have the disadvantage of being brittle or stiff, lacking the degree of flexibility and comfort most desired for movement of the skin, lips, and/or hair. Furthermore, the water-soluble nature of such film-formers or gelling agents has the additional disadvantage of making the applied film of product less water-resistant or waterproof, such that the applied film of product is too easily rubbed off or removed under such conditions as perspiration/sweating, washing, drinking, and swimming.

Other efforts have been directed to the inclusion of latexes or aqueous dispersions of film-forming polymer into the aqueous phase of O/W and W/O compositions. These film-forming polymer types produce water-resistant/waterproof films, and often have good flexibility on skin, lips, and/or hair. Some previous efforts, however, have required high levels of volatile organic compounds (e.g., lower alcohols) and/or plasticizing agents in the aqueous dispersion of polymer to achieve their intended film-formation effects. Such ingredients often have the disadvantage of being drying and/or irritating and/or damaging to the skin, lips, hair, and/or nails. Moreover, high levels of these ingredients typically impart offensive odors and/or taste to products, and cause the product to be flammable. Another limitation observed in previous efforts to effectively include these film-forming polymers into cosmetic compositions containing a fatty phase has been the requirement of one or more surfactants/emulsifying agents. Depending on the type and/or usage level of emulsifying agents, they can have the disadvantage of interfering with the adhesion or film-forming properties of the film-forming polymer, and/or producing an irritation or sensitization response in the skin, lips, or eyes. A further limitation encountered with the use of at least some aqueous dispersions of film-forming polymers is a susceptibility to rapid coagulation or polymer destabilization upon heating or addition to a heated fatty phase (typically above 40° C.).

More recently, efforts have been disclosed for improving long-wearing or transfer-resistant benefits by providing two-step cosmetic systems or kits. In the case of such systems or kits, a first cosmetic composition is applied to mammalian keratinous tissue to deliver a long-wearing/transfer-resistant film or layer that is allowed to set and/or dry, followed by application of a different second cosmetic composition over the first cosmetic composition. The second cosmetic composition is typically specified to be sufficiently different from the first cosmetic composition in chemical constituents or properties so as to prevent the long-wearing/transfer-resistant layer from being solubilized or compromised significantly. While the first cosmetic composition is long-wearing/transfer-resistant, it typically is deficient in appearance (i.e., has dull/matte finish) and/or feel (i.e., has dry, or rough/non-slippery feel). The purpose of the second cosmetic composition, therefore, is to contribute to the appearance (e.g., shine/gloss) and/or feel (e.g., lubricity) of the total applied system. These two-step systems or kits, however, have the disadvantage of being more complex and less convenient to use than a single long-wearing/transfer-resistant cosmetic composition. These systems or kits often have the further disadvantage of not retaining or sustaining a shiny/glossy appearance for an extended period of time.

Having thoughtfully considered the limitations and disadvantages encountered with previous efforts to provide long-lasting and/or transfer-resistant cosmetic compositions, and desiring especially to improve the maintenance of a lubricious/slippery and/or shiny/glossy appearance over time, it has now been discovered an improved novel long-wearing cosmetic compositions with improved gloss that overcome one or more of these limitations and disadvantages.

SUMMARY OF THE INVENTION

Cosmetic compositions of the present invention comprise:
(A) a first structured and adhesive film-forming fatty phase comprising:
  i) one or more lipidic components that are mutually compatible with one another when liquefied;
  ii) at least one adhesive film-forming agent; and
  iii) at least one lipophilic structuring agent in an amount effective to retain a second fatty phase entrapped in said cosmetic composition prior to application on mammalian keratinous tissue; and
(B) a second fatty phase comprising at least one non-volatile lipidic component; wherein said second fatty phase (B) is incompatible with said first structured and adhesive film-forming fatty phase (A) and said second fatty phase (B) is entrapped in said composition where upon application of said composition to mammalian keratinous tissue, said second fatty phase (B) readily separates from said composition to form a barrier layer over said first structured and adhesive film-forming fatty phase (A) and wherein said composition is substantially free of surfactants such that separation of said second fatty phase (B) from said composition is not prevented following application of said composition.

Methods of the present invention include, but are not limited to:

A method of providing long-lasting color and long-lasting shine simultaneously to mammalian keratinous tissue comprising the step of applying to said mammalian keratinous tissue a feel and shine enhancing barrier layer over a long-lasting color layer from a single cosmetic composition comprising:

(A) a first structured and adhesive film-forming fatty phase comprising:
  i. one or more lipidic components that are mutually compatible with one another when liquefied;
  ii. at least one adhesive film-forming agent; and
  iii. at least one lipophilic structuring agent in an amount effective to retain a second fatty phase entrapped in said cosmetic composition prior to application on mammalian keratinous tissue;
(B) a second fatty phase comprising at least one non-volatile lipidic component wherein said second fatty phase (B) is incompatible with said first structured and adhesive film-forming fatty phase (A) and said second fatty phase (B) is entrapped in said composition where upon application of said composition to mammalian keratinous tissue, said second fatty phase (B) readily separates from said composition to form a barrier layer over said first structured and adhesive film-forming fatty phase (A) and wherein said composition is substantially free of surfactants such that separation of said second fatty phase (B) from said composition is not prevented following application of said composition; and
(C) at least one coloring agent.

DETAILED DESCRIPTION OF THE INVENTION

While the specification concludes with the claims particularly pointing and distinctly claiming the invention, it is believed that the present invention will be better understood from the following description.

As used herein, "comprising" means that other steps and ingredients can be added. This term encompasses the terms "consisting of" and "consisting essentially of". The phrase "consisting essentially of" means that the composition may include additional ingredients, but only if the additional ingredients do not materially alter the basic and novel characteristics of the claimed compositions or methods.

All percentages, parts and ratios are based upon the total weight of the topical compositions of the present invention and all measurements made are at 25° C., unless otherwise specified. All such weights as they pertain to listed ingredients are based on the active level and, therefore, do not include carriers or by-products that may be included in commercially available materials, unless otherwise specified.

As used herein, the term "first phase" may be used as a substitute expression in referring to the "first structured and adhesive film-forming fatty phase" of the present invention.

As used herein, the term "second phase" may be used as a substitute expression in referring to the "second fatty phase" of the present invention.

As used herein, the term "mammalian keratinous tissue" refers to the skin, lips, hair (including eyelashes and eyebrows), and nails of mammalian subjects, especially humans.

As used herein, the term "non-volatile lipidic component" refers to any lipidic component that is liquid at room temperature (25° C.) and atmospheric pressure (760 mm Hg) having a vapor pressure less than about 5 mm Hg, preferably less than about 2 mm Hg, more preferably less than about 1 mm Hg, most preferably less than about 0 mm Hg.

By "incompatible" it is meant that the second phase is substantially or completely insoluble with the first phase, such that the second phase has little to no affinity or solubility with the first phase, and remains distinguishable from the first phase.

The term "surfactants" or "emulsifying agents," as used herein, refers to any surface-active agent (commonly referred to as surfactant) that has as its primary function the reduction of interfacial tension between two immiscible liquids to enable formation and stabilization of an emulsion. A surfactant generally consists of a molecule having a hydrophilic (water-loving) and lipophilic (oil-loving) part that migrates to and orients at the interface between immiscible liquids. For the purposes of this definition, such agents are considered distinct and separate from so-called auxiliary emulsifiers, i.e., "Emulsion Stabilizers" and "Viscosity-Increasing Agents" as defined in the *CTFA International Cosmetic Ingredient Handbook, Tenth Edition*, The Cosmetic, Toiletry, and Fragrance Association, Inc., 2004.

As used herein, "shine" refers to an ability to produce, or having the property of, brightness, luster, or radiance from the reflection of light at a surface. "Shine" encompasses the condition ranging from a subtle luster or sheen to a pronounced glistening or glossy, wet-like appearance.

(A) First Structured and Adhesive Film-Forming Fatty Phase

Compositions of the present invention comprise a first structured and adhesive film-forming fatty phase comprised of one or more mutually compatible lipidic components, at least one adhesive film-forming agent and at least one lipophilic structuring agent in an amount effective to retain a second fatty phase entrapped within the composition prior to application on mammalian keratinous tissue.

Compositions of the present invention comprise a first structured and adhesive film-forming fatty phase (i.e., first phase) present in an amount from at least about 30%, preferably from at least about 40%, more preferably from at least about 45%, even more preferably from at least about 50% and no more than about 95%, preferably no more than about 85%, more preferably no more than about 75%, even more preferably no more than about 65%, by weight of the total composition.

The primary purpose of the first structured and adhesive film-forming fatty phase in compositions of the present invention is to deliver a supple and/or glossy fatty phase with improved durability and long-wearing properties upon application to mammalian keratinous tissue. In preferred embodiments, this first structured and adhesive film-forming fatty phase also comprises one or more coloring agents so as to achieve long-lasting color and/or opacity upon application to mammalian keratinous tissue.

(i) Lipidic Components

The first structured and adhesive film-forming fatty phase is comprised of one or more lipidic components that are mutually compatible with one another when liquefied.

The term "lipidic component" refers to any lipophilic solvent, oil, fat, wax, fatty ester, fatty alcohol, fatty acid, silicone, lanolin or lanolin derivative, and any lipophilic polymeric or resinous material having predominately lipid-like properties that is insoluble or immiscible with water. Such materials may be derived from sources such as mineral, marine, animal, plant, and/or synthetic, and can be selected from polar and non-polar, volatile and non-volatile properties, and mixtures thereof, unless otherwise specified or limited in the description. This "lipidic component" may be in liquid state at room temperature (25° C.) and atmospheric pressure (760 mm Hg). Alternatively, it may be in paste, semi-solid or solid state (at room temperature and atmospheric pressure), and be capable of transforming to liquid state when heated above its melting point temperature (typically less than 100° C.) for the purpose of combining with other ingredients of the present invention.

As used herein, "mutually compatible with one another when liquefied" is defined as the condition wherein the liquefied components are soluble and miscible with one another, such that when blended together, they collectively form a single, homogeneous mixture that does not stratify or separate into distinct (discrete) phases or layers upon standing over time.

Lipidic components included in the first phase provide the capability to impart a variety of desirable attributes in such areas as application, feel, appearance, and conditioning attributes when applied to skin, lips, hair, and/or nails. Depending on the intended product use, these attributes may include, but are not necessarily limited to, ease of spreading, lubricity, emolliency, moisturization, and gloss. In cosmetic compositions lacking at least one lipidic component, such attributes generally cannot be achieved either at all or as effectively since water and/or many water-compatible ingredients are generally lacking in the chemical and/or physical properties necessary to impart such attributes to the product. Additionally, proper selection of the lipidic component for this phase also enables a variety of desired final product forms to be achieved, such as a liquid, cream, paste, or solid. The lipidic component also typically serves as a convenient and effective medium for dispersing and/or solubilizing other desirable optional ingredients that are compatible with the lipidic component, such as lipophilic moisturizers, vitamins, skin-active agents, skin care ingredients, coloring agents, thickeners, sunscreens, fragrances, flavors, preservatives and the like.

Lipidic components of the first structured and adhesive film-forming fatty phase may comprise from at least about 10%, preferably from at least about 15%, more preferably from at least about 20%, even more preferably from at least about 25% and no more than about 98.5%, preferably no more than about 97%, more preferably no more than about 95%, even more preferably no more than about 90%, by weight of the first structured and adhesive film-forming fatty phase.

Lipidic components of the first phase may exist in a liquid state at or about room temperature (25° C.). Such materials may be derived from sources such as mineral, marine, animal, plant, and/or synthetic and can be selected from polar and non-polar, volatile and non-volatile properties and mixtures thereof. As used herein, the term "volatile lipophilic liquid" refers to any lipophilic (or lipid-like) material that is liquid at room temperature (25° C.) and atmospheric pressure (760 mm Hg) having a measurable vapor pressure, greater than about 0 mm Hg, preferably greater than about 1 mm Hg, more preferably greater than about 2 mm Hg, most preferably greater than about 5 mm Hg.

In the present invention, volatile lipophilic liquids may be selected in particular to enhance the application and setting properties of an applied film on the skin, lips, hair, and/or nails. However, as was mentioned previously, compositions utilizing high levels of volatile oils/liquids typically produce films that feel dry and/or tight to the consumer, and appear dry (matte/dull) to the consumer. In certain product uses, most especially in the case of lipcolor and/or lipgloss, this is not particularly desirable or preferred. Therefore, depending on the intended product attributes or use sought, it may be preferable to limit use of volatile lipophilic liquids to be less than about 50% by weight of the total lipidic component of the first phase, preferably less than about 30% by weight of the total lipidic component of the first phase, more preferably less than about 20% by weight of the total lipidic component of the first phase, even more preferably less than about 10% by weight of the total lipidic component of the first phase, most preferably 0% by weight of the total lipidic component of the first phase.

Volatile lipophilic liquids may be selected from groups consisting of volatile hydrocarbon liquids, volatile silicone liquids, volatile fluorinated liquids, and mixtures thereof. These liquids may be selected from saturated and unsaturated, straight and branched chain, aliphatic, cycloaliphatic, and aromatic structures, and combinations thereof.

Non-limiting examples of volatile hydrocarbon liquids include C8-C16 isoalkanes (or isoparaffins) and branched C8-C16 esters, such as isododecane, isodecane, isohexadecane, isohexyl neopentanoate, and mixtures thereof.

Examples of volatile silicone liquids include, but are not limited to, volatile cyclic silicone liquids, such as octamethylcyclotetrasiloxane (D4), decamethylcyclopentasiloxane (D5), dodecamethylcyclohexasiloxane (D6), and combinations thereof; and volatile linear silicone liquids, such as octamethyltrisiloxane, heptamethyltrisiloxane, heptamethyloctyltrisiloxane, heptamethyl-hexyltrisiloxane, and mixtures thereof.

Examples of volatile fluorinated liquids include, but are not limited to, nonafluoromethoxybutane and perfluoromethylcyclopentane.

In the present invention, non-volatile lipophilic liquids may be selected in particular to enhance the lubricity, conditioning, and gloss/shine properties of an applied film on the skin, lips, hair, and/or nails. As used herein, the term "non-volatile lipophilic liquid" refers to any lipophilic (or lipid-like) material that is liquid at room temperature (25° C.) and atmospheric pressure (760 mm Hg) having a vapor pressure less than about 5 mm Hg, preferably less than about 2 mm Hg, more preferably less than about 1 mm Hg, most preferably less than about 0 mm Hg. In contrast to the aforementioned volatile oils/liquids, compositions utilizing high levels of non-volatile oils/liquids typically produce films that feel moist and/or soft and supple to the consumer, and appear wet or shiny/glossy to the consumer. In certain product uses, most especially in the case of lipcolor and/or lipgloss, this is particularly desirable or preferred. Therefore, depending on the intended product attributes or use sought, it may be preferable to maximize use of non-volatile lipophilic liquids to be more than about 50% by weight of the total lipidic component of the first phase, preferably more than about 70% by weight of the total lipidic component of the first phase, more preferably more than about 80% by weight of the total lipidic component of the first phase, even more preferably more than about 90% by weight of the total lipidic component of the first phase, most preferably 100% by weight of the total lipidic component of the first phase.

The total lipidic component of the first phase may be comprised of at least about 10% by weight, preferably at least about 30% by weight, more preferably at least about 60% by weight, even more preferably at least about 80% by weight, most preferably 100% by weight of one or more non-volatile lipophilic liquids having a refractive index (at 20° C.) of at least about 1.450, preferably at least about 1.460, more preferably at least about 1.470, even more preferably at least about 1.480, most preferably at least about 1.490.

As used herein, the "refractive index" of a substance is defined as the ratio of the velocity of light in air to the velocity of light in the substance. Typically, the values in the literature for refractive index are for the D line of sodium (doublet at 589.0 nm and 589.6 nm). The Abbe refractometer, or other refractometers of equal or greater accuracy, may be employed to measure the refractive index.

Non-volatile lipophilic liquids may be selected from groups consisting of non-volatile hydrocarbon liquids, non-volatile silicone liquids, non-volatile fluorinated liquids, and mixtures thereof. These liquids may be selected from saturated and unsaturated, straight and branched chain, aliphatic, cycloaliphatic, and aromatic structures, and combinations thereof.

Non-limiting examples of non-volatile hydrocarbon liquids include those of animal origin, such as lanolin oil; those of plant/vegetable origin, such as liquid triglycerides of fatty acids including triglycerides of heptanoic acid, triglycerides of octanoic acid, wheatgerm oil, corn oil, sunflower oil, shea butter oil, castor oil, sweet almond oil, macadamia oil, apricot oil, soybean oil, rapeseed oil, cotton oil, alfalfa oil, poppy oil, pumpkin oil, sesame oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passionflower oil, musk rose oil, and triglycerides of caprylic/capric acids; those of mineral and synthetic origin, such as liquid petrolatum, polydecenes, and hydrogenated polybutenes/polyisobutenes; synthetic esters and ethers, such as oils of the formula $R_1COOR_2$ wherein $R_1$ is selected from residues of higher fatty acids comprising from 6 to 29 carbon atoms and $R_2$ is selected from hydrocarbon chains comprising from 3 to 30 carbon atoms, such as cetostearyl octanoate, isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, and polyol esters, such as propylene glycol dioctanoate, neopentyl glycol diheptanoate, diethylene glycol diisononanoate, and pentaerythritol esters; liquid fatty alcohols comprising at least one carbon chain of 12 to 26 carbon atoms, such as octyldodecanol, isostearyl alcohol, oleyl alcohol, 2-hexyldecanol, 2-butyloctanol, and 2-undecylpentadecanol; higher fatty acids, such as myristic acid, palmitic acid, stearic acid, behenic acid, oleic acid, linoleic acid, linolenic acid, and isostearic acid; and mixtures thereof.

Examples of non-volatile silicone liquids include, but are not limited to, polydimethylsiloxanes (PDMSs) comprising groups selected from alkyl, alkoxy, and phenyl groups that are pendant and/or at the end of the silicone chain and containing from 2 to 24 carbon atoms; phenyl silicones, such as phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane; and mixtures thereof.

Examples of non-volatile fluorinated liquids include, but are not limited to, fluorinated silicones, such as perfluorononyl dimethicones.

In order to prepare products that are more occlusive, viscous, and/or structured (including semi-solid and solid product forms), one or more of the lipidic components may comprise a lipidic solid forming material in an amount sufficient to thicken and/or solidify the composition into a desired product form. These lipidic solid formers may be used in the present invention provided they are used at levels that do not significantly interfere with the adhesive film-forming properties of the adhesive film-forming agent included in the first structured and adhesive film-forming fatty phase. Said solid formers are selected from the group consisting of solid polyol fatty acid polyesters, waxes, solid oils, and mixtures thereof.

The solid polyol fatty acid polyesters suitable for use in the first phase of the present invention include those solid polyol fatty acid polyester materials described in U.S. Pat. No. 6,555,097 issued to Rabe et al., on Apr. 29, 2003.

Waxes are defined as organic mixtures or compounds of high molecular weight, solid at room temperature (25° C.) and generally similar in composition to fats and oils except that they contain no glycerides. Included are high molecular weight hydrocarbons, fatty acids, fatty acid esters, fatty alcohols, and mixtures thereof. Waxes useful in the present invention are selected from those generally known in the art.

Suitable high molecular weight fatty acids have from about 10 to about 40 carbon atoms. Examples include, but are not limited to, 12-hydroxystearic acid, 12-hydroxylauric acid, 16-hydroxyhexadecanoic acid, behenic acid, stearic acid, caprylic acid, lauric acid, and mixtures thereof. Further examples of some suitable fatty acids are described in U.S. Pat. No. 5,429,816 issued to Hofrichter et al., on Jul. 4, 1995; and U.S. Pat. No. 5,552,136 issued to Motley on Sep. 3, 1996.

Suitable high molecular weight fatty acid esters include ester waxes, monoglycerides, diglycerides, triglycerides, and mixtures thereof. Non-limiting examples of suitable ester waxes include stearyl stearate, stearyl behenate, palmityl stearate, cetearyl behenate, and behenyl behenate. Specific examples of these include CRODAMOL SS from Croda and the KESTER WAXES from Koster Keunen.

Suitable high molecular weight fatty alcohols include monohydric alcohols having from about 20 to about 40 carbon atoms, and do not perform as primary emulsifiers, such as the PERFORMACOLS® from New Phase Technologies.

Other waxes useful in the fatty phase of the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point greater than about 30° C. The waxes most useful herein have melting points from about 30° C. to about 115° C.

Waxes suitable for use include, but are not limited to, beeswax, lanolin wax, shellac wax (animal waxes); carnauba, candelilla, bayberry (vegetable waxes); ozokerite, ceresin (mineral waxes); paraffin, microcrystalline waxes (petroleum waxes); polyethylene (ethylenic polymers) and polyethylene homopolymers (Fischer-Tropsch waxes); C30-45 alkyl methicones/dimethicones from Dow Coming and General Electric, KP-560P series of acrylic silicone copolymers from Shin-Etsu Silicones (silicone waxes); and mixtures thereof.

Other waxes useful in the present invention are selected from the group consisting of jojoba esters such as the FLORAESTERS® sold by Floratech Americas, PERFORMALENE™ polyethylenes and PERFORMA V™ synthetic polymers sold by New Phase Technologies, alkylated polyvinylpyrrolidines sold under tradename GANEX® from International Specialty Products, SYNCROWAXES® sold by Croda, fatty alcohols from C22 to C50, and mixtures thereof. Synthetic waxes include those disclosed in Warth, *Chemistry and Technology of Waxes*, Part 2, 1956, Reinhold Publishing. The waxes useful herein are selected from the $C_8$ to $C_{50}$ hydrocarbon waxes. Such waxes include long chained polymers of ethylene oxide combined with a dihydric alcohol, namely polyoxyethylene glycol. Such waxes include CARBOWAX™ available from Carbide and Carbon Chemicals Company. Other synthetic waxes include long-chained polymers of ethylene with OH or other stop length grouping at end of chain. Such waxes include the Fischer-Tropsch waxes as disclosed in the text disclosed above at pages 465-469 and include ROSSWAX™, available from Ross company and PT-0602 available from Astor Wax Company.

Solid oils useful herein are those that have a melting point from above about 30° C., preferably above about 37° C. and no more than below about 250° C., preferably no more than below about 100° C., even more preferably no more than below about 80° C. As used herein, the term "solid oils" refers to any oil or oil-like material that is solid or semi-solid at temperatures of from about 20° C. to about 25° C., and has a solubility in water of generally less than about 1% by weight at 25° C. Examples of suitable solid oils include, but are not limited to, petrolatum, highly branched hydrocarbons, fatty alcohols, fatty acid esters, vegetable oils, hydrogenated vegetable oils, polypropylene glycols, alpha-hydroxy fatty acids, fatty acids having from about 10 to about 40 carbon atoms, alkyl amides of di- and/or tri-basic carboxylic acids, n-acyl amino acid derivatives, and mixtures thereof. Solid oils useful in the fatty phase of the present invention are further described in U.S. Pat. No. 4,919,934, to Deckner et al., issued Apr. 24, 1990.

Suitable highly branched hydrocarbons for use herein include hydrocarbon compounds having from about 17 to about 40 carbon atoms. Non-limiting examples of these hydrocarbon compounds include squalane, cholesterol, lanolin, docosane (i.e., a C22 hydrocarbon), and isoparaffins.

Vegetable oils and hydrogenated vegetable oils that are solid or semi-solid at temperatures from about 20° C. to about 25° C. are also useful herein. Examples of suitable vegetable oils and hydrogenated vegetable oils include, but are not limited to, babassu oil, cocoa butter, coconut oil, palm oil, palm kernel oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, hydrogenated macadamia oil, derivatives thereof and mixtures thereof.

Suitable polypropylene glycols for use herein include C4-C16 alkyl ethers of polypropylene glycols, and C1-C16 carboxylic acid esters of polypropylene glycols. Non-limiting examples of these materials include PPG-14 butyl ether, PPG-15 stearyl ether, PPG-9, PPG-12, PPG-15, PPG-17, PPG-20, PPG-26, PPG-30, PPG-34, and mixtures thereof.

Suitable alkyl amides of di- and/or tri-basic carboxylic acids for use herein include disubstituted or branched monoamides, monosubstituted or branched diamides, triamides, and mixtures thereof. Some specific examples of alkyl amides of di- and tri-basic carboxylic acids include, but are not limited to, alkyl amides of citric acid, tricarballylic acid, aconitic acid, nitrilotriacetic acid, and itaconic acid such as 1,2,3-propane tributylamide, 2-hydroxy-1,2,3-propane tributylamide, 1-propene-1,2,3-trioctylamide, N,N',N"-tri(methyldecylamide)amine, 2-dodecyl-N,N'-dibutylsuccinamide, and mixtures thereof. Other suitable amides include the n-acylamino acid derivatives described in U.S. Pat. No. 5,429,816, issued to Hofrichter et al., on Jul. 4, 1995.

(ii) Adhesive Film-Forming Agent

The first structured and adhesive film-forming fatty phase is comprised of at least one adhesive film-forming agent.

As used herein, "adhesive film-forming agent" refers to any polymeric or resinous material or mixtures thereof capable of forming a solid film and having adhesive qualities upon subsequent treatment (i.e., chemical and/or energy-induced transformations) and/or elimination of the liquid component (i.e., liquid evaporation and/or absorption) from the polymeric or resinous material or mixtures. The adhesive film-forming agent may be one material or an aggregate of materials dissolved or dispersed within the first structured and adhesive film-forming fatty phase. Alternatively, the adhesive film-forming agent may be one material or an aggregate of materials that form a distinct polymeric or resinous "phase" distinguishable within the first structured and adhesive film-forming fatty phase. If such adhesive film-forming agent is considered a polymeric or resinous phase, such phase can be distinguished from the second fatty phase of the present invention that is entrapped within the composition of the present invention. Polymeric or resinous materials form solid films through one or more transformation processes, including, but not necessarily limited to, particle coalescence, fusion, sintering, polymer chain entanglement/interdiffusion, and/or chemical cross-linking reaction. Such transformation processes may occur in response to chemical stimuli, including, but not necessarily limited to, pH changes, oxidation reactions, and hydration. Such transformation processes may also occur in response to energetic stimuli, including, but not necessarily limited to, heat and ultraviolet (UVA/UVB) energy. Alternatively, the transformation processes may occur in response to evaporation and/or absorption of liquid component from the polymeric or resinous material.

Adhesive film-forming agents of the first structured and adhesive film-forming fatty phase comprise from at least about 1%, preferably from at least about 3%, more preferably from at least about 5%, even more preferably from at least about 7% and no more than about 60%, preferably no more than about 50%, more preferably no more than about 45%, even more preferably no more than about 35%, by weight of the first structured and adhesive film-forming fatty phase.

The at least one adhesive film-forming agent may be lipophilic and oil-soluble (herein after referred to as Lipo-Soluble), lipophilic and oil-dispersible (herein after referred to as Lipo-Dipsersible), hydrophilic and water-soluble (herein after referred to as Hydro-Soluble), or hydrophilic and water-dispersible (herein after referred to as Hydro-Dispersible). The term "oil-soluble" means that the adhesive film-forming agent is soluble or miscible in oils and lipidic liquids, and will form a single homogeneous phase when incorporated therein. The term "oil-dispersible" means that the adhesive film-forming agent is dispersible in oils and lipidic liquids, and will form an insoluble phase where the dispersed adhesive film-forming agent remains stable and/or compatible when incorporated therein. The term "water-soluble" means that the adhesive film-forming agent is soluble or miscible in water, and will form a single homogeneous phase when incorporated therein. The term "water-dispersible" means that the adhesive film-forming agent is dispersible in water, and will form an insoluble phase where the dispersed adhesive film-forming agent remains stable and/or compatible when incorporated therein.

Any type of adhesive film-forming agent may be used so long as they remain soluble or dispersible in, and compatible with, only the first structured and adhesive film-forming fatty phase of the present invention. Adhesive film-forming agents may be derived from natural or synthetic sources.

Adhesive film-forming agents of the present invention may be produced and/or used in a dry, particulate, or powdered form. Alternatively, they may be produced and/or used in a pre-solubilized or solution form where the polymeric or resinous material is dissolved in one or more solvents. Alternatively, they may be produced and/or used in a stabilized dispersion form where the polymeric or resinous material is dispersed and stabilized as particles in one or more liquids.

Specific adhesive film-forming agents are selected based on the particular properties and requirements sought for the intended use. Such properties and requirements include, but are not limited to, film flexibility or hardness, adhesiveness, toughness or durability, and resistance to water or other chemical insults. It is also possible, and many times preferable, to take advantage of the more versatile properties achievable in block copolymers (polymers comprised of two or more distinct polymer block segments), graft copolymers (polymers having pendant polymeric side chains grafted onto a homopolymer or copolymer backbone) or heteropolymers (polymers comprised of two or more different monomers) instead of homopolymers. In block type copolymers, the type and amount of "soft" and "hard" segments have a significant impact on performance properties.

Moreover, it is possible in compositions of the present invention to combine two or more different adhesive film-forming agents together to achieve benefits of blended or synergistic properties. Examples of different combinations include, but are not necessarily limited to, polyurethanes with polyacrylates; and polyurethanes with polyesters.

Without being limited by theory, adhesive film-forming agents used in compositions of the present invention may have linear, branched, or partially cross-linked polymer chains, and may be selected from groups consisting of homopolymers, heteropolymers, copolymers and mixtures thereof. The polymers may be anionic, cationic, nonionic, or amphoteric in nature. Particularly preferred are the anionic and/or nonionic heteropolymers and/or copolymers.

Preferred adhesive film-forming agents of the present invention may be formed by chain-growth (free-radical) polymerization processes (so called addition polymers), and/or step-growth polymerization processes (so called condensation polymers).

Among the chain-growth or free-radical class of polymers, the adhesive film-forming agent may be selected from the group consisting of acrylic polymers and copolymers, vinyl polymers and copolymers, vinyl-acrylic copolymers, styrene-acrylic copolymers, silicone-acrylics, and mixtures thereof. Anionic free-radical polymers are particularly preferred. Vinyl and/or acrylic polymers can result from monomers with ethylenic unsaturation having at least one acid group, and/or esters of acidic monomers, and/or amides of acidic monomers. Particularly preferred among the monomers with ethylenic unsaturation having at least one acid group are those selected from acrylic acid, methacrylic acid, crotonic acid, and maleic acid. Preferable among the esters of acidic monomers are those selected from (meth)acrylates, in particular, alkyl (meth)acrylates, aryl (meth)acrylates, and hydroxyalkyl (meth)acrylates. Included among the alkyl (meth)acrylates, for example, are methyl methacrylate, ethyl methacrylate, butyl methacrylate, isobutyl methacrylate, 2-ethylhexyl methacrylate, and lauryl methacrylate. Included among the aryl (meth)acrylates, for example, are benzyl acrylate and phenyl acrylate. Included among the hydroxyalkyl (meth)acrylates, for example, are hydroxyethyl acrylate, 2-hydroxypropyl acrylate, hydroxyethyl methacrylate, and 2-hydroxypropyl methacrylate. Preferable among the amides of acidic monomers are those selected from (meth)acrylamides, in particular, N-alkyl (meth)acrylamides. Included among the N-alkyl (meth)acrylamides, for example, are N-ethyl acrylamide, N-t-butyl acrylamide, and N-t-octyl acrylamide.

Vinyl and/or acrylic polymers can also result from vinyl ester and styrene monomers. These monomers can be polymerized with acidic monomers, and/or esters of acidic monomers, and/or amides of acidic monomers such as those discussed above. Preferable among the vinyl esters are vinyl acetate, vinyl neodecanoate, vinyl pivalate, vinyl benzoate, and vinyl t-butyl benzoate. The listing of monomers given above is not intended to be limiting and other monomers known to those skilled in the art of preparing these chain-growth polymers may be utilized.

Among the step-growth class of polymers, the adhesive film-forming agents may be selected from the group consisting of polyurethanes, polyureas, polyurea-polyurethanes, polyester-polyurethanes, polyether-polyurethanes, polyvinylpyrrolidone-polyurethanes, acrylic-polyurethanes, silicone-polyurethanes, polyesters, polyamides, polyesteramides, epoxy ester resins, and mixtures thereof. Among the polyurethanes, the "soft" block segments are comprised of polyols that are typically polyethers or polyesters that can range from low to high molecular weight. The polyethers and polyesters may be linear and/or branched aliphatic, and/or cycloaliphatic, and/or aromatic in nature. The "hard" block segments are comprised of the diisocyanates (that can be aromatic, aliphatic, and/or cycloaliphatic), and chain extender amines (that can be diamines or polyamines of aliphatic or aromatic nature). Preferred among these are the anionic and/or nonionic versions of the polyurethanes and polyurethane hybrid copolymer classes listed above. Particularly preferred are the polyether-polyurethanes and polyester-polyurethanes.

Suitable adhesive film-forming agents also include natural gums and extracts selected from, but not limited to, the group consisting of plant exudates, such as gum arabic, gum tragacanth, gum karaya, and gum ghatti; plant extracts, such as pectins; plant seed flours or extracts, such as locust bean gum, guar gum, psyllium seed gum, and quince seed gum; seaweed extracts, such as agar, alginates, and carrageenans; seed starches, such as corn starch, wheat starch, rice starch, and sorghum starch; tuber starches, such as tapioca starch and potato starch; animal extracts, such as gelatin and caseinates; and mixtures thereof.

Additional suitable adhesive film-forming agents include modified (semi-synthetic) gums and extracts selected from, but not limited to, the group consisting of cellulose derivatives, such as sodium carboxymethylcellulose, hydroxyethylcellulose, hydroxypropylcellulose, methylcellulose, and hydroxypropyl methylcellulose, as well as alkyl-modified cellulose derivatives, such as cetyl hydroxyethylcellulose; modified plant extracts, such as hydroxypropyl guar; microbial or biosynthetic gums, such as xanthan gum, sclerotium gum, gellan gum, dextran and its derivatives; modified starches and starch derivatives, such as potato starch modified, corn starch modified, hydroxypropyl starch, dextrin and its derivatives; modified animal derivatives, such as chitin or chitosan, and their derivatives, collagen derivatives; and mixtures thereof.

Additional suitable adhesive film-forming agents include, but are not limited to, organic silicone resins (e.g., trimethylsiloxysilicate such as SR1000 from GE Silicones) and copolymers of organic silicone resins (e.g., diisostearyl trimethylolpropane siloxy silicate such as SF1318 from GE Silicones); fluorinated silicone resins; acrylic and/or vinyl based polymers or copolymers, including silicone and/or fluorinated versions (e.g., the "KP" series of silicone acrylates from Shin-Etsu Silicones, and 3M™ Silicones "Plus" Polymer VS70 and SA70); polyurethanes (e.g., the hydroxyester triglyceride derived Polyderm® series from Alzo International); polyesters (e.g., the Lexorez® series of polymeric polyesters from Inolex Chemical Company); and mixtures thereof.

Addition and Preparation of Adhesive Film-Forming Agent

Combination of at least one adhesive film-forming agent with at least one lipidic component and at least one lipophilic structuring agent of the first structured and adhesive film-forming fatty phase may be achieved by any means known to those skilled in the art, such that the film-forming agent is uniformly dissolved and/or dispersed throughout the first structured and adhesive film-forming fatty phase. In some cases, it may be more efficient or effective to introduce the adhesive film-forming agent gradually over a period of time into one or more of the lipidic components or lipophilic structuring agents while under the influence of continuous mixing. Any suitable means of addition, mixing, or temperature conditions may be used to facilitate combination of the specific ingredients and satisfy manufacturing needs, provided the conditions do not significantly disrupt adhesion or film-forming properties of the adhesive film-forming agent.

In the particular case for Hydro-Soluble adhesive film-forming agents, they may be first solubilized in a liquid medium comprised of water and/or hydrophilic materials (such as glycols and low chain-length alcohols), added as a solution form into one or more of the lipidic components or lipophilic structuring agents while under the influence of continuous mixing, and stabilized as an emulsified or dispersed phase with the aid of one or more emulsifying agents. However, if one or more emulsifying agents are used for stabilizing Hydro-Soluble adhesive film-forming agents as a dispersed or emulsified phase, such emulsifying agents must not interfere with separation of the second fatty phase from the composition upon application of said composition to mammalian keratinous tissue.

In the particular case for Hydro-Dispersible adhesive film-forming agents, such as those made into latexes or aqueous dispersions of adhesive film-forming polymer particles, they may be first dispersed in a liquid medium comprised of water and/or hydrophilic materials (such as glycols and low chain-length alcohols), added as a stable dispersion form into one or more of the lipidic components or lipophilic structuring agents while under the influence of continuous mixing, and stabilized as an emulsified or dispersed phase with the aid of one or more emulsifying agents. However, if one or more emulsifying agents are used for stabilizing Hydro-Dispersible adhesive film-forming agents as a dispersed or emulsified phase, such emulsifying agents must not interfere with separation of the second fatty phase from the composition upon application of said composition to mammalian keratinous tissue.

In particularly preferred embodiments, Hydro-Dispersible adhesive film-forming agents may be prepared as a Structured Aqueous Polymeric Adhesive Phase, and subsequently combined with one or more of the lipidic components and/or lipophilic structuring agents according to the further description provided below.

(a) Structured Aqueous Polymeric Adhesive Phase

In compositions of the present invention, a structured aqueous polymeric adhesive phase is comprised of (1) at least one aqueous dispersion of adhesive film-forming polymer particles; and (2) at least one structuring agent in an amount effective to viscoelastically thicken, but not solidify, the structured aqueous polymeric adhesive phase to be compatible when combined with one or more lipidic components of the first phase.

As used herein, "aqueous dispersion of adhesive film-forming polymer particles" refers to polymer dispersed and suspended as particles in an aqueous phase or medium, these particles being capable of coalescing together to form an adhesive film on the skin, hair, or nails upon evaporation or absorption of the aqueous phase. Formation and stabilization of these polymer particle dispersions in an aqueous medium may be achieved using means such as synthetic procedures characterized as: (1) polymer synthesized in the presence of water (e.g., emulsion polymerization); and (2) polymer synthesized in the bulk, or in solution with an organic solvent, and subsequently dispersed in water. In preferred embodiments, the aqueous phase or medium consists essentially of water, or a mixture of water and non-volatile water-miscible solvents. Non-volatile water-miscible solvents may be included only to the extent that they do not significantly disrupt the performance of the aqueous polymeric adhesive phase of the present invention. As used herein, "non-volatile water-miscible solvents" refers to any non-aqueous solvent capable of being mixed in water without separation, having a slower evaporation rate than water at room temperature and relative humidity (25° C., R.H. 50%) and atmospheric pressure (760 mm Hg).

The term "structuring agent" as used herein refers to any naturally- or synthetically-derived material that, when combined in an effective amount with an aqueous dispersion of adhesive film-forming polymer particles, produces a viscoelastic thickening response that results in a thixotropic or pseudoplastic structure. "Viscoelastic" refers to the condition in which a material has a combination of viscous (liquid-like) and elastic (solid-like) properties, being neither completely viscous nor completely elastic in response to deformation stresses. The term "thixotropic" as used herein means the viscosity decreases when the structure is subjected to increasing shear rate followed by a time-dependent partial or total recovery of the starting viscosity when the shear rate is decreased or removed. The term "pseudoplastic" as used herein means the viscosity decreases when the structure is subjected to increasing shear rate but a time-independent or instantaneous total recovery of the starting viscosity occurs when the shear rate is decreased or removed. By means of capillary forces and/or physicochemical interactions at the molecular level, the structuring agent is capable of readily absorbing, dissolving in, being wetted by, and/or otherwise interacting with the aqueous phase and polymer particles of the aqueous dispersion of film-forming polymer particles to impart a significant increase in viscosity and viscoelastic structure to the structured aqueous polymeric adhesive phase.

The term "but not solidify" as used herein means the structured aqueous polymeric adhesive phase is not structured to the point of being essentially rigid or solid. As used herein, being "essentially rigid or solid" is defined from a dynamic oscillatory rheometry measurement in the Linear Viscoelastic Region (more fully disclosed later in the detailed description and test methods) as the condition wherein the Elastic Modulus (G') is greater than the Viscous Modulus (G") for any oscillation frequency less than or equal to 1 Hz.

By "compatible" it is meant that the structured aqueous polymeric adhesive phase is capable of existing and performing as an adhesive phase in agreeable combination with the first phase and/or forming a homogeneous composition wherein the structured aqueous polymeric adhesive phase does not readily separate from the first phase after being combined.

The term "thermally-tolerant" as used herein means having the ability to withstand exposure to temperature at least about 15° C. below and above room temperature (25° C.) for brief (minutes to hours) and/or extended (hours to days) periods and still remain compatible and function effectively within the composition. Although the extent of thermal tolerance will be dependent upon such factors as the character and amounts of film-forming polymer and structuring agent, preferred compositions of the present invention have demonstrated an ability to withstand exposure to temperatures as high as about 90° C., and temperatures as low as about −5° C.

Compositions of the present invention may comprise a structured aqueous polymeric adhesive phase wherein at least one aqueous dispersion of adhesive film-forming polymer particles is combined with an effective amount of at least one structuring agent. In contrast, cosmetic compositions using an aqueous dispersion of adhesive film-forming polymer particles wherein a structuring agent is either absent or combined at less than effective structuring levels, typically would be incompatible when combined with lipidic components unless one or more effective emulsifying agents were also included. The present invention, however, does not require an emulsifying agent as a means of achieving compatibility between the lipidic components of the first phase and the aqueous dispersion of adhesive film-forming polymer particles within the structured aqueous polymeric adhesive phase. This is advantageous because it avoids the potential problem of skin irritation or sensitization that may occur with some types of emulsifying agents. Further, the present invention avoids the potential problem of emulsifying agents destabilizing the polymer particles or interfering with their adhesive and/or film-forming properties.

When a structured aqueous polymeric adhesive phase is used as an adhesive film-forming agent in compositions of the present invention, their purpose is to simultaneously achieve viscoelastic structuring, compatibility, thermal-tolerance, and adhesive film-forming properties within the first structured and adhesive film-forming fatty phase of the composition. The combination of viscoelastic structuring and adhesive film-forming properties when combined or dispersed within the first phase enables the first phase to better resist migration from the intended application area and to better withstand physical and chemical insults (such as rubbing, washing, drinking, and eating) that would typically cause removal of an applied film from the skin, hair, or nails. The aqueous medium, however, also provides a means to more easily incorporate desirable optional ingredients that are compatible with the aqueous medium, such as water-soluble moisturizers, vitamins, skin-active agents, skin care ingredients, coloring agents, preservatives, and the like. Said materials may be used provided their inclusion does not significantly disrupt the compatibility or long-wearing properties of the composition once the composition has been applied wherein a film has been formed on the skin, lips, hair or nails.

The total level of structured aqueous polymeric adhesive phase of the present invention may be present from at least about 1%, preferably from at least about 3%, more preferably from at least about 5%, even more preferably from at least about 7% and no more than about 60%, preferably no more than about 50%, more preferably no more than about 45%, even more preferably no more than about 35%, by weight of the first structured and adhesive film-forming fatty phase.

Combination of the structuring agent with an aqueous dispersion of adhesive film-forming polymer particles may be achieved by any means known to those skilled in the art, such that the structuring agent is uniformly distributed and dispersed throughout the structured aqueous polymeric adhesive phase, producing the intended thickening or structuring effect. In most cases, it is more efficient or effective to introduce the structuring agent gradually over a period of time into an aqueous dispersion of adhesive film-forming polymer particles while under the influence of continuous mixing. Any suitable means of addition, mixing, or temperature conditions may be used to facilitate combination of the specific ingredients and satisfy manufacturing needs, provided the conditions do not significantly disrupt adhesion or film-forming properties of the polymer, or significantly disrupt intended performance of the structuring agent. Attainment of the completed state for this phase may be determined by any appropriate means known to those skilled in the art for the specific ingredient combination selected. A viscometer, or more preferably, a rheometer is well-suited for determining the completed state.

In addition to imparting an adhesive film-forming capacity to the first phase of the present invention, the structured aqueous polymeric adhesive phase imparts beneficial structuring, compatibility, and thermal-tolerance to the composition that cannot be achieved either at all or as effectively when using an aqueous dispersion of adhesive film-forming polymer particles alone. Compositions using an aqueous dispersion of adhesive film-forming polymer particles wherein a structuring agent is either absent or combined at less than effective levels, are typically more vulnerable to migration away from the intended application area, removal forces, and other insults following application. In these cases, an applied composition often lacks sufficient structural integrity to resist migration and/or degradation until such time as evaporation/absorption of the aqueous medium has effectively allowed final polymer film-formation processes to occur. During this time, portions of the applied composition can often migrate and/or be removed by insults, further reducing the availability and effectiveness of the remaining portion to provide the intended benefits to the skin, hair, and/or nails. This is particularly the situation observed where the lipidic component of the first phase is comprised either entirely or predominately of non-volatile liquids, especially low viscosity non-volatile liquids. In compositions of the present invention, however, the desired increased resistance to migration and deformation is achieved by the viscosity and thixotropic/pseudoplastic structure formed within the structured aqueous polymeric adhesive phase, as well as by physicochemical interaction forces between phase boundaries of the structured aqueous polymeric adhesive phase and the remaining components comprising a first phase of the present invention. These effects are responsible for a significant enhancement to the long-wearing capacity of aqueous dispersions of adhesive film-forming polymers.

Finally, it has been discovered in the present invention that effective structuring of the structured aqueous polymeric adhesive phase also provides improved tolerance to both hot and cold temperatures. The thermal tolerance permits a wider range of lipidic components (i.e., those requiring heat to be liquefied) to be included in the first phase of the present invention. Moreover, it enables compositions of the present invention to more effectively withstand processing and storage temperatures. Without being limited by theory, the reason for this improved thermal tolerance is believed to be the result of colloidal stabilization of the adhesive film-forming polymer particles by the structuring agent, where the increased viscosity and/or interceding presence of the structuring agent among the film-forming polymer particles effectively inhibits the ease or rate of polymer coagulation that typically occurs at high (greater than 40° C.) and/or low temperatures (less than 0° C.). Although the extent of thermal tolerance will be dependent upon such factors as the character and amounts of film-forming polymer and structuring agent, preferred embodiments of the present invention have demonstrated an ability to withstand exposure to temperature as high as 90° C., and temperature as low as −5° C.

As previously stated, the structured aqueous polymeric adhesive phase has a viscoelastic structure that is distinctly pseudoplastic or thixotropic in nature. This viscoelastic structure provides both a shear-induced thinning behavior and a strong viscosity recovery mechanism to the composition. In preferred embodiments of the present invention, the composition recovers to at least about 20%, preferably to at least about 25%, more preferably to at least about 30%, even more preferably to at least about 35%, most preferably to at least about 40% of its starting viscosity when shear rate is decreased to zero or removed.

In preferred embodiments of the present invention, the structured aqueous polymeric adhesive phase has a pseudoplastic or near-pseudoplastic structure that is responsible for imparting the viscosity recovery mechanism to the composition. In particularly preferred embodiments, the structured aqueous polymeric adhesive phase recovers to at least about 70%, preferably to at least about 80%, more preferably to at least about 90%, even more preferably to at least about 95%, most preferably to about 100% of its starting viscosity when shear rate is decreased to zero or removed.

It has been discovered in the present invention that the shear-thinning and viscosity recovery characteristics significantly influence the application and long-wear properties of the composition. At low shear rates (e.g., less than $10\,s^{-1}$), the structured aqueous polymeric adhesive phase not only has a higher viscosity when compared to its viscosity at high shear rates (e.g., greater than $200\,s^{-1}$), but also has an ability to quickly recover to a high viscosity after being subjected to high shear rates. Hence, at low shear rates or stresses, the composition benefits with increased structural integrity and resistance to deformation or migration caused by low stress forces (e.g., gravity). This is particularly advantageous in low stress or shear conditions (such as storage) for enhancing composition stability, as well as after application of the composition to skin, lips, hair, and/or nails for reducing the tendency of an applied film to migrate or be easily disturbed or removed. A structured aqueous polymeric adhesive of the present invention has a viscosity (25° C.) at low shear rates (i.e., in the range $1\,s^{-1}$-$10\,s^{-1}$) from at least about 2 Pa-s (2,000 cP), preferably from at least about 4 Pa-s (4,000 cP), more preferably from at least about 5 Pa-s (5,000 cP), even more preferably from at least about 6 Pa-s (6,000 cP), most preferably from at least about 7 Pa-s (7,000 cP) and no more than about 60 Pa-s (60,000 cP), preferably no more than about 50 Pa-s (50,000 cP), more preferably no more than about 45 Pa-s (45,000 cP), even more preferably no more than about 40 Pa-s (40,000 cP), most preferably no more than about 35 Pa-s (35,000 cP).

Conversely, at high shear rates (e.g., greater than $200\,s^{-1}$), the structured aqueous polymeric adhesive phase has a significantly lower viscosity than its viscosity at low shear rates. Hence, at high shear rates or stresses, the composition benefits with lower resistance to deformation and flow. And this is particularly advantageous in high shear conditions such as dispensing and filling operations, as well as during product application conditions such as spreading, rubbing, or brushing. A structured aqueous polymeric adhesive of the present invention has a viscosity (25° C.) at high shear rates (i.e., in the range $400\,s^{-1}$-$500\,s^{-1}$) from at least about 0.5 Pa-s (500 cP), preferably from at least about 1 Pa-s (1,000 cP), more preferably from at least about 1.5 Pa-s (1,500 cP) and no more than about 5 Pa-s (5,000 cP), preferably no more than about 4 Pa-s (4,000 cP), more preferably no more than about 3 Pa-s (3,000 cP).

Steady shear rheometry measurements known in the art can be performed to characterize this viscosity response as a function of increasing shear for the structured aqueous polymeric adhesive phase. These viscosity responses can be determined by performing a controlled rate rotation ramp using the instrumentation and methodology described later in the section entitled "Test Methods".

In order to more fully define and describe the viscoelastic properties sought for the structured aqueous polymeric adhesive phase, dynamic oscillatory rheometry measurements, a common technique known in the art, can be performed to characterize the Elastic Modulus (G') (solid-like response) and Viscous Modulus (G") (liquid-like response) of the structured aqueous polymeric adhesive phase. The "Linear Viscoelastic Region" (LVR) is defined as the region of applied oscillatory shear stress where there is a linear relationship between stress and strain, resulting in moduli that are constant or nearly constant within this applied shear stress region. These moduli responses can be determined by performing dynamic oscillatory stress sweeps using the instrumentation and methodology described later in the section entitled "Test Methods". The term "yield stress," as used herein, is defined as the stress required to initiate flow, and can be identified from a dynamic oscillatory stress sweep as the critical stress at which the LVR is exceeded.

A structured aqueous polymeric adhesive of the present invention has an Elastic Modulus (G') (25° C.) in the Linear Viscoelastic Region (LVR) at a fixed oscillation frequency of 1 Hz from at least about 5 Pa, preferably from at least about 7 Pa, more preferably from at least about 9 Pa, even more preferably from at least about 10 Pa and no more than about 100 Pa, preferably no more than about 80 Pa, more preferably no more than about 60 Pa, even more preferably no more than about 50 Pa.

A structured aqueous polymeric adhesive of the present invention has a Viscous Modulus (G") (25° C.) in the Linear Viscoelastic Region (LVR) at a fixed oscillation frequency of 1 Hz from at least about 15 Pa, preferably from at least about 20 Pa, more preferably from at least about 30 Pa, even more preferably from at least about 35 Pa and no more than about 300 Pa, preferably no more than about 250 Pa, more preferably no more than about 200 Pa, even more preferably no more than about 180 Pa.

The ratio of G"/G' (or tan δ) in the LVR at a fixed oscillation frequency of 1 Hz for a structured aqueous polymeric adhesive phase is from at least about 1.5, preferably from at least about 2.0, more preferably from at least about 2.5 and no more than about 5.5, preferably no more than about 5, more preferably no more than about 4.5.

The yield stress at a fixed oscillation frequency of 1 Hz for a structured aqueous polymeric adhesive phase is from at least about 10 Pa, preferably from at least about 15 Pa, more preferably from at least about 20 Pa and no more than about 400 Pa, preferably no more than about 350 Pa, more preferably no more than about 300 Pa.

(1) Aqueous Dispersion of Adhesive Film-Forming Polymer Particles

In compositions of the present invention, a structured aqueous polymeric adhesive phase is comprised of at least one aqueous dispersion of adhesive film-forming polymer particles.

For example, the level of adhesive film-forming particles may be present from at least about 0.5%, preferably from at least about 1%, more preferably from at least about 3% and no more than about 30%, preferably no more than about 20%, more preferably no more than about 15%, by weight of the total composition.

In preferred embodiments of the present invention, the structured aqueous polymeric adhesive phase and/or aqueous dispersion of adhesive film-forming polymer particles are substantially free of volatile organic components. The term "substantially free of volatile organic components" means the aqueous phase contains little or no volatile organic compounds, such as low boiling point alcohols or other Volatile Organic Compounds (VOC) as defined by the U.S. Environmental Protection Agency (40 CFR Part 51 Section 51.100 Definitions, as of August 2000). Preferably, the presence of volatile organic compounds is no more than about 10%, preferably no more than about 5%, more preferably no more than about 1%, most preferably no more than about 0% (trace/impurity level), by weight of the composition.

Polymers of the present invention may be formed by chain-growth (free-radical) polymerization processes (so called addition polymers), and/or step-growth polymerization processes (so called condensation polymers). Formation and stabilization of these polymer particle dispersions in an aqueous medium may be achieved using means such as synthetic procedures characterized as: (1) polymer synthesized in the presence of water (e.g., emulsion polymerization); and (2) polymer synthesized in the bulk, or in solution with an organic solvent, and subsequently dispersed in water. More detailed reviews and descriptions of these polymerization processes can be found in the published literature, such as *Waterborne Coatings: Emulsion and Water-Soluble Paints*, Charles R. Martens, Van Nostrand Reinhold Company, 1981; *Polyurethane Handbook, Second Edition*, Gunter Oertel, Ed., Hanser Gardner Publications, 1994; and *Technology for Waterborne Coatings*, J. Edward Glass, Ed., American Chemical Society, 1997.

Anionic, cationic, or nonionic stabilized aqueous polymer dispersions can be used in compositions of the present invention. Anionic dispersions are generally more widely used and preferred to cationic dispersions due to the greater stability of anionic dispersions and very small particle sizes achievable. A limiting feature of anionic polymer dispersions that are stabilized solely by ionized carboxylic acid or sulphonic acid groups is that they become unstable at low pH (i.e., below the pKa of the stabilizing acid group). Nonionically stabilized dispersions, on the other hand, are more stable towards freezing, pH changes, and addition of electrolytes, but to achieve small particle sizes, a high concentration of polyethylene oxide based co-monomer is required which can introduce undesirable water sensitivity into the final film. Thus, combinations of anionic and nonionic stabilizations can be used to obtain a synergistic effect, whereby a combination of small particle size and steric stability against freezing, pH changes, and electrolytes can be achieved, without the need for excessive concentrations of polyethylene oxide co-monomer. Polymer dispersions utilizing this type of stabilization can be, for example, blended with low pH, acid containing acrylic copolymers.

Specific adhesive film-forming polymers are selected based on the particular properties and requirements sought for the intended use. Such properties and requirements include, but are not limited to, film flexibility or hardness, adhesiveness, toughness or durability, and resistance to water or other chemical insults. It is also possible, and many times preferable, to take advantage of the more versatile properties achievable in block copolymers (polymers comprised of two or more distinct polymer block segments) or heteropolymers (polymers comprised of two or more different monomers) instead of homopolymers. In block type copolymers, the type and amount of "soft" and "hard" segments have a significant impact on performance properties.

Moreover, it is possible in compositions of the present invention to combine two or more different aqueous dispersions of adhesive film-forming polymer particles together to achieve benefits of blended or synergistic polymer properties. Examples of different combinations include, but are not necessarily limited to, polyurethanes with polyacrylates; and polyurethanes with polyesters.

Without being limited by theory, the adhesive film-forming polymers used in compositions of the present invention may have linear, branched, or partially cross-linked polymer chains, and may be selected from groups consisting of homopolymers, heteropolymers, copolymers and mixtures thereof. The polymers may be anionic, cationic, nonionic, or amphoteric in nature. Particularly preferred are the anionic and/or nonionic heteropolymers and/or copolymers.

Among the chain-growth or free-radical class of polymers, the adhesive film-forming polymers may be selected from the group consisting of acrylic polymers and copolymers, vinyl polymers and copolymers, vinyl-acrylic copolymers, styrene-acrylic copolymers, silicone-acrylics, and mixtures thereof. Anionic free-radical polymers are particularly preferred. Vinyl and/or acrylic polymers can result from monomers with ethylenic unsaturation having at least one acid group, and/or esters of acidic monomers, and/or amides of acidic monomers. Particularly preferred among the monomers with ethylenic unsaturation having at least one acid group are those selected from acrylic acid, methacrylic acid, crotonic acid, and maleic acid. Preferable among the esters of acidic monomers are those selected from (meth)acrylates, in particular, alkyl (meth)acrylates, aryl (meth)acrylates, and hydroxyalkyl (meth)acrylates. Included among the alkyl (meth)acrylates, for example, are methyl methacrylate, ethyl methacrylate, butyl methacrylate, isobutyl methacrylate, 2-ethylhexyl methacrylate, and lauryl methacrylate. Included among the aryl (meth)acrylates, for example, are benzyl acrylate and phenyl acrylate. Included among the hydroxyalkyl (meth)acrylates, for example, are hydroxyethyl acrylate, 2-hydroxypropyl acrylate, hydroxyethyl methacrylate, and 2-hydroxypropyl methacrylate. Preferable among the amides of acidic monomers are those selected from (meth)acrylamides, in particular, N-alkyl (meth)acrylamides. Included among the N-alkyl (meth)acrylamides, for example, are N-ethyl acrylamide, N-t-butyl acrylamide, and N-t-octyl acrylamide.

Vinyl and/or acrylic polymers can also result from vinyl ester and styrene monomers. These monomers can be polymerized with acidic monomers, and/or esters of acidic monomers, and/or amides of acidic monomers such as those discussed above. Preferable among the vinyl esters are vinyl acetate, vinyl neodecanoate, vinyl pivalate, vinyl benzoate, and vinyl t-butyl benzoate. The listing of monomers given above is not intended to be limiting and other monomers known to those skilled in the art of preparing these chain-growth polymers may be utilized.

Among the step-growth class of polymers, the adhesive film-forming polymers may be selected from the group consisting of polyurethanes, polyureas, polyurea-polyurethanes, polyester-polyurethanes, polyether-polyurethanes, polyvinylpyrrolidone-polyurethanes, acrylic-polyurethanes, silicone-polyurethanes, polyesters, polyamides, polyesteramides, epoxy ester resins, and mixtures thereof. Among the polyurethanes, the "soft" block segments are comprised of polyols that are typically polyethers or polyesters that can range from low to high molecular weight. The polyethers and polyesters may be linear and/or branched aliphatic, and/or cycloaliphatic, and/or aromatic in nature. The "hard" block segments are comprised of the diisocyanates (that can be aromatic, aliphatic, and/or cycloaliphatic), and chain extender amines (that can be diamines or polyamines of aliphatic or aromatic nature). Preferred among these are the anionic and/or nonionic versions of the polyurethanes and polyurethane hybrid copolymer classes listed above. Particularly preferred are the polyether-polyurethanes and polyester-polyurethanes.

The level of adhesive film-forming polymer particles dispersed in the aqueous dispersion of film-forming polymer particles of the present invention is from at least about 10%, preferably from at least about 20%, more preferably from at least about 30% and no more than about 50%, preferably no more than about 45%, more preferably no more than about 40% of the total weight percent of the aqueous dispersion of adhesive film-forming polymer particles.

The average size of adhesive film-forming polymer particles (as determined by dynamic light scattering methods known in the art) dispersed in the aqueous dispersion of film-forming polymer particles is from at least about 5 nm, preferably from at least about 10 nm and no more than about 800 nm, preferably no more than about 500 nm, more preferably no more than about 300 nm, even more preferably no more than about 100 nm.

The weight average molecular weight (as determined by gel permeation chromatography) of polymer dispersed in the aqueous dispersion of film-forming polymer particles is preferably from at least about 10,000, more preferably from at least about 15,000, even more preferably from at least about 20,000 and preferably no more than about 200,000, more preferably no more than about 100,000, even more preferably no more than about 50,000.

(2) Structuring Agent

In compositions of the present invention, a structured aqueous polymeric adhesive phase is comprised of at least one structuring agent. Specifically, the structuring agent is present from at least about 0.01%, preferably from at least about 0.03%, more preferably from at least about 0.05% and no more than about 5%, preferably no more than about 3%, more preferably no more than about 2%, by weight of the total composition.

The structuring agent performs several essential functions when combined with an aqueous dispersion of adhesive film-forming polymer particles. First, the hydrophilic and/or water-induced thickening response of the structuring agent reduces the amount of "free" or mobile water in the structured aqueous polymeric adhesive phase of the present invention. It accomplishes this by binding it as water of hydration or solvation for the structuring agent, and immobilizing water within the thickened structure. Using an effective amount of structuring agent prevents separation and/or inhibits migration of the water from the structured aqueous polymeric adhesive phase of the present invention. Second, the interaction forces established among water, structuring agent, and adhesive film-forming polymer particles are responsible for increasing viscosity and viscoelasticity of the structured aqueous polymeric adhesive phase. The free movement or rearrangement of polymer particles usually occurring in an aqueous dispersion of film-forming polymer particles is thus inhibited in the structured aqueous polymeric adhesive phase. A distinctly pseudoplastic or thixotropic profile is produced that enables both shear-thinning behavior and a strong viscosity recovery, the advantages of which were previously discussed. Third, the structuring behavior imparts improved thermal tolerance for an aqueous dispersion of adhesive film-forming polymer particles in combination with a first phase. These functions enable desired compatibility of a structured aqueous polymeric adhesive phase when combined with the first phase, as well as achieve long-wearing properties of the present invention.

Consideration must be given to several factors in selecting the type of structuring agent best suited to a specific composition. Such factors include, but are not necessarily limited to, compatibility with the ionic-nature of the particular adhesive film-forming polymer particles, temperature conditions in processing the composition, sensitivity to pH level or changes, and sensitivity to electrolytes or dissolved salts. A person skilled in the art will recognize the relative importance of these and other such factors in selecting an appropriate structuring agent to satisfy the essential functions listed above. Importantly, a person skilled in the art will realize that the degree of structuring and pseudoplasticity or thixotropy can be adjusted by proper selection of the type and quantity of structuring agents to satisfy desired level and/or quality of application, feel, durability, appearance, and stability properties intended for the final composition.

In preferred embodiments, the structuring agent is capable of imparting its structuring effect when the pH is from about 4, preferably from about 5, more preferably from about 6 and no more than about 10, preferably no more than about 9.

In additional preferred embodiments, the structuring agent is capable of maintaining and/or recovering its structuring effect following exposure to temperature greater than about 40° C., preferably greater than about 50° C., more preferably greater than about 60° C., even more preferably greater than about 70° C., most preferably greater than about 80° C.

Particularly, the structuring agent of the present invention is selected from the group consisting of natural gums and extracts, modified (semi-synthetic) gums and extracts, hydrophilic natural and synthetic silicate and clay mineral agents, hydrophobic silicas, inorganic and polymeric porous microparticle absorbents, synthetic polymers (such as acrylic polymers), and mixtures thereof.

Natural gums and extracts of the present invention are selected from, but not limited to, the group consisting of plant exudates, such as gum arabic, gum tragacanth, gum karaya, and gum ghatti; plant extracts, such as pectins; plant seed flours or extracts, such as locust bean gum, guar gum, psyllium seed gum, and quince seed gum; seaweed extracts, such as agar, alginates, and carrageenans; seed starches, such as corn starch, wheat starch, rice starch, and sorghum starch; tuber starches, such as tapioca starch and potato starch; animal extracts, such as gelatin and caseinates; and mixtures thereof.

Modified (semi-synthetic) gums and extracts of the present invention are selected from, but not limited to, the group consisting of cellulose derivatives, such as sodium carboxymethylcellulose, hydroxyethylcellulose, hydroxypropylcellulose, methylcellulose, and hydroxypropyl methylcellulose, as well as alkyl-modified cellulose derivatives, such as cetyl hydroxyethylcellulose; modified plant extracts, such as hydroxypropyl guar; microbial or biosynthetic gums, such as xanthan gum, sclerotium gum, gellan gum, dextran and its derivatives; modified starches and starch derivatives, such as potato starch modified, corn starch modified, hydroxypropyl starch, dextrin and its derivatives; modified animal derivatives, such as chitin or chitosan, and their derivatives, collagen derivatives; and mixtures thereof.

Hydrophilic natural and synthetic clay mineral agents of the present invention are selected from, but not limited to, the group consisting of hectorites, such as those sold under tradenames BENTONE® (Elementis Specialties); bentonites and montmorillonites, such as those sold under tradenames OPTIGEL® (Sud-Chemie), GELWHITE® and MINERAL COLLOID® (both by Southern Clay Products), and POLAR-GEL® (AMCOL Health & Beauty Solutions); magnesium aluminum silicates, such as those sold under tradenames VEEGUM® (R.T. Vanderbilt Company), MAGNABRITE® (AMCOL Health & Beauty Solutions), and GELWHITE® MAS (Southern Clay Products); sodium magnesium silicate, such as those sold under tradenames OPTIGEL® SH (Sud-Chemie) and LAPONITE® (Southern Clay Products); lithium magnesium sodium silicate, such as LUCENTITE® SWN (Kobo Products); lithium magnesium silicate, such as LUCENTITE® SAN (Kobo Products); and mixtures thereof.

Hydrophobic silicas of the present invention are selected from, but not limited to, the group consisting of hydrophobically modified fumed silicas, such as WACKER HDK® H15, H20, and H30 (Wacker-Chemie), and hydrophobic grades under tradenames of AEROSIL® (Degussa AG) and CAB-O-SIL® (Cabot Corporation); and mixtures thereof.

Inorganic and polymeric porous microparticle absorbents of the present invention are selected from, but not limited to, the group consisting of high porosity/void volume fumed silicas, such as MSS-5003H and Silica Shells (both sold by Kobo Products), high porosity/void volume silicates like calcium silicate, such as sold under tradename HUBERDERM™ (J.M. Huber Corporation); high porosity/void volume polymeric particle absorbents including methacrylate polymers like allyl methacrylates copolymer, sold as POLYPORE® E-200 (AMCOL Health & Beauty Solutions), and cross-linked dimethacrylate copolymers like lauryl methacrylate/glycol dimethacrylate crosspolymer sold as POLYTRAP® 6603 (Enhanced Derm Technologies); high porosity cellulose beads like Cellulobeads® (Kobo Products); and mixtures thereof.

Synthetic polymers of the present invention include, but are not limited to, acrylic polymers, such as polyacrylates and polymethacrylates, and acrylic copolymers and crosspolymers, such as the carbomers or acrylates/C1O-C30 alkyl acrylate crosspolymers sold under tradename CARBOPOL® (Noveon), and sodium polyacrylate sold under tradename RAPITHIX™ A-100 (International Specialty Products); alkali-soluble/swellable emulsion (ASE) polymers, hydrophobically-modified alkali-soluble/swellable emulsion (HASE) polymers, and hydrophobically-modified ethoxylated urethane (HEUR) polymers, such as those sold under tradename ACULYNT™ (Rohm and Haas Company) and STRUCTURE® (National Starch and Chemical Company); hydrophobically-modified ethoxylate urethane alkali-soluble/swellable emulsion (HUERASE) polymers, such a those sold under tradename UCAR® POLYPHOBE® (Union Carbide Corporation); copolymers of methyl vinyl ether and maleic anhydride, such as PVM/MA decadiene crosspolymer sold under tradename STABILEEZE® (International Specialty Products); hydrophobically modified nonionic associative thickeners such as those sold under tradename PURE-THIX® (Sud-Chemie); and mixtures thereof.

Preferred structuring agents of the present invention are those capable of achieving and maintaining the most consistent structuring and compatibility performance across a range of pH and/or electrolyte conditions, as well as temperature conditions. Particularly preferred are those from the groups of modified (semi-synthetic) gums and extracts, especially the cellulose derivatives, hydrophilic natural and synthetic clay mineral agents, and synthetic polymers.

Compositions of the present invention may comprise at least one structuring agent in an amount effective to viscoelastically thicken, but not solidify, the structured aqueous polymeric adhesive phase of the present invention to be compatible with the first structured and adhesive film-forming fatty phase of the present invention. However, it is possible, and in some situations may be more preferable, in compositions of the present invention to use two or more structuring agents together in the structured aqueous polymeric adhesive phase in order to achieve the benefit of blended or synergistic properties for viscosity, compatibility, thermal-tolerance, or stability.

(iii) Lipophilic Structuring Agent

Compositions of the present invention comprise at least one lipophilic structuring agent in an amount effective to retain the second fatty phase entrapped in said cosmetic composition prior to application on mammalian keratinous tissue.

Lipophilic structuring agents of the first structured and adhesive film-forming fatty phase comprise from at least about 0.50%, preferably from at least about 1%, more preferably from at least about 2%, even more preferably from at least about 4% and no more than about 60%, preferably no more than about 50%, more preferably no more than about 40%, even more preferably no more than about 30%, by weight of the first structured and adhesive film-forming fatty phase.

The term "lipophilic structuring agent" as used herein refers to any naturally- or synthetically-derived material having lipophilic tendency that provides a thickening or firming action resulting in a gelled, paste-like, semi-solid, or solid structure in the first phase. By means of one or more physicochemical interactions with one or more components that comprise the first phase, a lipophilic structuring agent imparts a significant increase in viscosity and/or resistance to an applied stress or deformation force. Examples of these physicochemical interactions include, but are not limited to, liquid absorption, particle swelling, particle networking/flocculation, crystallization, hydrogen bond bridging, polymer chain entanglement, and coagulation. Preferred structures are those that retain sufficient viscosity/firmness to prevent premature separation of the second phase from the composition at various storage temperatures (e.g., from about 0° C. to about 50° C.) prior to application, but efficiently collapse, breakdown, or become shear-thinning upon application to mammalian keratinous tissue. The structure may demonstrate no measurable recovery whatsoever following application (i.e., irreversible structure loss), or may be thixotropic or pseudoplastic. The term "thixotropic" as used herein means the viscosity decreases when the structure is subjected to increasing shear rate followed by a time-dependent partial or total recovery of the starting viscosity when the shear rate is decreased or removed. The term "pseudoplastic" as used herein means the viscosity decreases when the structure is subjected to increasing shear rate but a time-independent or instantaneous total recovery of the starting viscosity occurs when the shear rate is decreased or removed.

Lipophilic structuring agents of the present invention may be derived from sources such as mineral, marine, animal, plant, and/or synthetic, and can be selected from polar and non-polar properties, and mixtures thereof. They may be in paste, semi-solid or solid state (at room temperature and atmospheric pressure), and be capable of transforming to liquid state when heated above its melting point temperature (typically less than 100° C.) for the purpose of combining with the first structured and adhesive film-forming fatty phase.

In order to prepare products that are more viscous and/or structured (including semi-solid and solid product forms), one or more of the lipophilic structuring agents may comprise a lipidic solid forming material in an amount sufficient to thicken and/or solidify so as to retain the second phase entrapped in the composition prior to application. These lipidic solid formers may be used in the present invention provided they are used at levels that do not significantly interfere with the adhesive film-forming properties of the adhesive film-forming agent included in the first structured and adhesive film-forming fatty phase. Said solid formers are selected from the group consisting of solid polyol fatty acid polyesters, waxes, solid oils, and mixtures thereof.

The solid polyol fatty acid polyesters suitable for use in the present invention include those solid polyol fatty acid polyester materials described in U.S. Pat. No. 6,555,097 issued to Rabe et al., on Apr. 29, 2003.

Waxes are defined as organic mixtures or compounds of high molecular weight, solid at room temperature (25° C.) and generally similar in composition to fats and oils except that they contain no glycerides. Included are high molecular weight hydrocarbons, fatty acids, fatty acid esters, fatty alcohols, and mixtures thereof. Waxes useful in the present invention are selected from those generally known in the art.

Suitable high molecular weight fatty acids have from about 10 to about 40 carbon atoms. Examples include, but are not limited to, 12-hydroxystearic acid, 12-hydroxylauric acid, 16-hydroxyhexadecanoic acid, behenic acid, stearic acid, caprylic acid, lauric acid, and mixtures thereof. Further examples of some suitable fatty acids are described in U.S. Pat. No. 5,429,816 issued to Hofrichter et al., on Jul. 4, 1995; and U.S. Pat. No. 5,552,136 issued to Motley on Sep. 3, 1996.

Suitable high molecular weight fatty acid esters include ester waxes, monoglycerides, diglycerides, triglycerides, and mixtures thereof. Non-limiting examples of suitable ester waxes include stearyl stearate, stearyl behenate, palmityl stearate, cetearyl behenate, and behenyl behenate. Specific examples of these include CRODAMOL SS from Croda and the KESTER WAXES from Koster Keunen.

Suitable high molecular weight fatty alcohols include monohydric alcohols having from about 20 to about 40 carbon atoms, and do not perform as primary emulsifiers, such as the PERFORMACOLS™ from New Phase Technologies.

Other waxes useful in the fatty phase of the present invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point greater than about 30° C. The waxes most useful herein have melting points from about 30° C. to about 115° C.

Waxes suitable for use include, but are not limited to, beeswax, lanolin wax, shellac wax (animal waxes); carnauba, candelilla, bayberry (vegetable waxes); ozokerite, ceresin (mineral waxes); paraffin, microcrystalline waxes (petroleum waxes); polyethylene (ethylenic polymers) and polyethylene homopolymers (Fischer-Tropsch waxes); C30-45 alkyl methicones/dimethicones from Dow Corning and General Electric, KP-560P series of acrylic silicone copolymers from Shin-Etsu Silicones (silicone waxes); and mixtures thereof.

Other waxes useful in the present invention are selected from the group consisting of jojoba esters such as the FLORAESTERS® sold by Floratech Americas, PERFORMALENE™ polyethylenes and PERFORMA V™ synthetic polymers sold by New Phase Technologies, alkylated polyvinylpyrrolidines sold under tradename GANEX® from International Specialty Products, SYNCROWAXES® sold by Croda, fatty alcohols from C22 to C50, and mixtures thereof. Synthetic waxes include those disclosed in Warth, *Chemistry and Technology of Waxes*, Part 2, 1956, Reinhold Publishing. The waxes useful herein are selected from the $C_8$ to $C_{50}$ hydrocarbon waxes. Such waxes include long chained polymers of ethylene oxide combined with a dihydric alcohol, namely polyoxyethylene glycol. Such waxes include CARBOWAX™ available from Carbide and Carbon Chemicals company. Other synthetic waxes include long-chained polymers of ethylene with OH or other stop length grouping at end of chain. Such waxes include the Fischer-Tropsch waxes as disclosed in the text disclosed above at pages 465-

469 and include ROSSWAX™, available from Ross company and PT-0602 available from Astor Wax Company.

Solid oils useful herein are those that have a melting point from above about 30° C., preferably above about 37° C. and no more than below about 250° C., preferably no more than below about 100° C., even more preferably no more than below about 80° C. As used herein, the term "solid oils" refers to any oil or oil-like material that is solid or semi-solid at temperatures of from about 20° C. to about 25° C., and has a solubility in water of generally less than about 1% by weight at 25° C. Examples of suitable solid oils include, but are not limited to, petrolatum, highly branched hydrocarbons, fatty alcohols, fatty acid esters, vegetable oils, hydrogenated vegetable oils, polypropylene glycols, alpha-hydroxy fatty acids, fatty acids having from about 10 to about 40 carbon atoms, alkyl amides of di- and/or tri-basic carboxylic acids, n-acyl amino acid derivatives, and mixtures thereof. Solid oils useful in the fatty phase of the present invention are further described in U.S. Pat. No. 4,919,934, to Deckner et al., issued Apr. 24, 1990.

Suitable highly branched hydrocarbons for use herein include hydrocarbon compounds having from about 17 to about 40 carbon atoms. Non-limiting examples of these hydrocarbon compounds include squalane, cholesterol, lanolin, docosane (i.e., a C22 hydrocarbon), and isoparaffins.

Vegetable oils and hydrogenated vegetable oils that are solid or semi-solid at temperatures from about 20° C. to about 25° C. are also useful herein. Examples of suitable vegetable oils and hydrogenated vegetable oils include, but are not limited to, babassu oil, cocoa butter, coconut oil, palm oil, palm kernel oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, hydrogenated macadamia oil, derivatives thereof and mixtures thereof.

Suitable polypropylene glycols for use herein include C4-C16 alkyl ethers of polypropylene glycols, and C1-C16 carboxylic acid esters of polypropylene glycols. Non-limiting examples of these materials include PPG-14 butyl ether, PPG-15 stearyl ether, PPG-9, PPG-12, PPG-15, PPG-17, PPG-20, PPG-26, PPG-30, PPG-34, and mixtures thereof.

Suitable alkyl amides of di- and/or tri-basic carboxylic acids for use herein include disubstituted or branched monoamides, monosubstituted or branched diamides, triamides, and mixtures thereof. Some specific examples of alkyl amides of di- and tri-basic carboxylic acids include, but are not limited to, alkyl amides of citric acid, tricarballylic acid, aconitic acid, nitrilotriacetic acid, and itaconic acid such as 1,2,3-propane tributylamide, 2-hydroxy-1,2,3-propane tributylamide, 1-propene-1,2,3-trioctylamide, N,N',N''-tri(methyldecylamide)amine, 2-dodecyl-N,N'-dibutylsuccinamide, and mixtures thereof. Other suitable amides include the n-acylamino acid derivatives described in U.S. Pat. No. 5,429,816, issued to Hofrichter et al., on Jul. 4, 1995.

Additional suitable lipophilic structuring agents useful for the present invention include, but are not limited to, organically modified clays, fumed silica, trihydroxystearin, silicone gels or silicone elastomers, and mixtures thereof.

Organically modified clays useful for the present invention include, but are not limited to, organically modified versions of hectorite, bentonite, smectite and montmorillonite clay (such as those sold under tradename BENTONE® from Elementis Specialties, TIXO-GEL® from Sud-Chemie, and CLAYTONE® from Southern Clay Products). Hydrophilically modified fumed silicas include, but are not limited to, WACKER HDK® N20 and T30 grades (Wacker-Chemie), and hydrophilic grades under tradename of AEROSIL® (Degussa AG). Silicone gels or silicone elastomers include, but are not limited to, the "KSG" thickening series (KSG-15, KSG-16, KSG-18, KSG-41, KSG-42, KSG-43, KSG-44) from Shin-Etsu Silicones, DOW CORNING®9040, 9041, 9045, and 9546 silicone elastomer blends from Dow Corning, SFE839™, SFE818™, and Velvesil™ silicone gels from GE Silicones, and WACKER-BELSIL® RG-100 from Wacker-Chemie.

(B) Second Fatty Phase

The composition of the present invention comprises a second fatty phase that is incompatible with the first structured and adhesive film-forming fatty phase, and entrapped in the composition. By "incompatible" it is meant that the second phase is substantially or completely insoluble with the first phase, such that the second phase has little to no affinity or solubility with the first phase, and remains distinguishable from the first phase. This second phase remains dispersed and entrapped throughout the composition until the composition experiences shearing forces created by application of the composition on mammalian keratinous tissue. At this point, the dispersed second phase is released or escapes from the composition, so that the second phase coalesces and spreads over the layer of first phase, essentially forming a barrier layer.

The second fatty phase provides the composition with a medium capable of delivering a glossy and protective barrier layer that separates from the composition upon application, forming a barrier layer over the first phase deposited on mammalian keratinous tissue. Depending on the intended product use, this separating barrier layer can significantly improve ease of spreading, lubricity, emolliency, moisturization for enhanced feel and gloss attributes for the composition.

The second fatty phase of the present invention is present from at least about 5%, preferably from at least about 15%, more preferably from at least about 25%, even more preferably from at least about 35% and no more than about 70%, preferably no more than about 60%, more preferably no more than about 55%, even more preferably no more than about 50% by weight of the total composition.

The second fatty phase of the present invention comprises at least one non-volatile lipidic component. The second fatty phase may have a viscosity from about 1 cSt, preferably from about 5 cSt, more preferably from about 10 cSt and no more than about 5,000 cSt, preferably no more than about 3,000 cSt, more preferably no more than about 1,000 cSt.

The at least one non-volatile lipidic component of the second fatty phase is in a liquid state at or about room temperature (25° C.). The lipidic materials of the second fatty phase may be derived from sources such as mineral, marine, animal, plant, and/or synthetic, and can be selected from polar and non-polar properties, and mixtures thereof, so long as they are sufficiently incompatible with the first phase so as to readily separate from the composition upon application.

The second fatty phase preferably is close to being optically transparent or clear, and colorless or low in color so as to have the maximum effect on gloss and/or least effect on color observation for the applied layer of first structured and adhesive film-forming fatty phase.

The second fatty phase comprises one or more lipidic components that are incompatible with the first structured and adhesive film-forming fatty phase.

It should be noted, however, some of the individual components making up the first phase and second phase may exhibit some degree of compatibility with components of the opposite phase. Volatile oils are one such example of a component that may partition between the first and second phases. However, in the present invention, any component demonstrating at least some compatibility for both the first and second phases will not exhibit compatibility to the degree that its inclusion makes the first and second phases completely compatible with one another. Furthermore, while the second phase is incompatible with the first phase, the second phase may be an aggregate of materials wherein some and possibly all of those materials are incompatible with each other.

The existence of a second fatty phase entrapped within the composition is readily detectable by an artisan using routine analytical methods, including using centrifugation, microscopy, or other means.

To enable the spreading of the second fatty phase over the surface, it is beneficial that the second fatty phase separates from the composition and easily spreads over the first structured and adhesive film-forming fatty phase layer by routine application without receding back into or forming individual droplets over the first layer. The ability of a second fatty phase to spread and remain in such a state is determined by the surface tension of the second fatty phase and by the surface tension of the underlying first layer. The second fatty phase is found to be spreadable over a surface when its surface tension is equal to or below the critical surface tension for wetting the surface. The critical surface tension for wetting a surface, first defined by Fox and Zisman, is equal to the surface tension of the second fatty phase which just exhibits a zero contact angle on the surface; see H. W. Fox and W. A. Zisman, J. Colloid Sci., 5, 514 (1950), H. W. Fox and W. A. Zisman, J. Colloid Sci., 7, 109 (1952) and H. W. Fox and W. A. Zisman, J. Colloid Sci., 7, 428 (1952). Since this critical surface tension of wetting can vary with composition of the first phase, a second fatty phase with a surface tension equal to or below the critical surface tension of wetting may be chosen for each particular first phase composition. Such a second fatty phase will exhibit a contact angle of about zero when placed on a flat, drawn-down film of the compositions first phase. The surface tension of the second fatty phase of the present invention is less than about 35 dynes/cm, preferably less than about 30 dynes/cm, most preferably less than about 25 dynes/cm.

In the present invention, non-volatile lipophilic liquids may be selected in particular to enhance the lubricity, conditioning, and gloss/shine properties of an applied film on the skin, lips, hair, and/or nails. In contrast to volatile oils/liquids, compositions utilizing high levels of non-volatile oils/liquids typically produce films that feel moist and/or soft and supple to the consumer, and appear wet or shiny/glossy to the consumer. In certain product uses, most especially in the case of lipcolor and/or lipgloss, this is particularly desirable or preferred.

In a preferred embodiment, the total lipidic component of the second fatty phase is comprised of at least about 10% by weight, preferably at least about 30% by weight, more preferably at least about 60% by weight, even more preferably at least about 80% by weight, most preferably 100% by weight of one or more non-volatile lipophilic liquids having a refractive index (at 20° C.) of at least about 1.450, preferably at least about 1.460, more preferably at least about 1.470, even more preferably at least about 1.480, most preferably at least about 1.490.

Non-volatile lipophilic liquids for the second fatty phase may be selected from groups consisting of non-volatile hydrocarbon liquids, non-volatile silicone liquids, non-volatile fluorinated liquids, and mixtures thereof. These liquids may be selected from saturated and unsaturated, straight and branched chain, aliphatic, cycloaliphatic, and aromatic structures, and combinations thereof.

Preferred non-volatile lipophilic liquids useful in the present invention include poly(organosiloxane) fluids, poly(phenylmethylsiloxane) fluids, poly(fluoroalkylmethlysiloxane) fluids, perfluoropolyethers, the copolymers of said fluids, and mixtures thereof.

Non-limiting examples of non-volatile silicone liquids include, but are not limited to, polydimethylsiloxanes (PDMSs) comprising groups selected from alkyl, alkoxy, phenyl, and fluoroalkyl groups that are pendant and/or at the end of the silicone chain and containing from 2 to 24 carbon atoms; phenyl silicones, such as phenyl trimethicones, phenyl dimethicones, phenyl trimethylsiloxydiphenylsiloxanes, diphenyl dimethicones, diphenyl methyldiphenyl trisiloxanes, 2-phenylethyl trimethylsiloxysilicates, trimethyl pentaphenyl trisiloxane; and mixtures thereof.

Examples of non-volatile fluorinated liquids include, but are not limited to, fluorinated silicones, such as perfluorononyl dimethicones, and the perfluoropolyethers commercially available under the Fomblin HC series.

Optional Ingredients

Compositions of the present invention may also comprise one or more of the following optional ingredients including, but not limited to, coloring agents, fillers/bulking agents, active agents and mixtures thereof.

Coloring Agents

Coloring agents suitable for use herein include all inorganic and organic colors/pigments, including mineral or pearl pigments suitable for use in cosmetic compositions. Such coloring agents include those either with or without a surface coating or treatment.

Compositions of the present invention may contain at least one coloring agent in an amount sufficient to provide the type and intensity of coloration, and/or light scattering, and/or light reflecting effects sought by the user for a particular product. Without being limited by theory, the coloring agents are used herein at levels of up to about 20% by weight relative to the total composition, and are included in the first structured and adhesive film-forming fatty phase of the present invention.

Preferred inorganic pigments include titanium dioxide (anatase or rutile forms), zinc oxide, iron oxides, ferric ammonium ferrocyanide, manganese violet, ultramarine blue, and chromium oxide green.

Organic colors/pigments are usually aluminum, barium, calcium, or strontium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Those certified by the Food and Drug Administration of the United States of America under the FD&C and/or D&C designations are particularly preferred.

Preferred lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake, Red 30 Talc Lake, and Red 30 Aluminum Lake.

Other coloring agents can also be included in the compositions, such as dyes bearing the FD&C and/or D&C designations, including Red 6, Red 21, Red 27, Blue 1, Orange 5, and Green 5 dyes. Preferred mineral and pearl pigments include both white and colored pigments. Examples of white mineral and pearl pigments include titanated micas (mica covered with titanium dioxide), and bismuth oxychloride. Examples of colored mineral and pearl pigments include titanated micas with iron oxides, titanated micas with organic colors, titanated micas with chromium or aluminum oxide, titanated micas with ferric ammonium ferrocyanide, and titanated micas with carmine.

Fillers/Bulking Agents

Fillers suitable for use in the first structured and adhesive film-forming fatty phase may be inorganic or organic, and be incorporated as complementary ingredients to help maintain more consistent coloring and/or performance properties in the compositions. Examples of such fillers/bulking agents include, but are not limited to, talc, mica, silica, boron nitride, polymeric powders such as those made of Nylon®, polytetrafluoroethylene (PTFE), polyethylene, acrylate polymers/copolymers like polymethyl methacrylate (PMMA), and silicone powders like polymethylsilsesquioxane (such as sold under tradename TOSPEARL® from GE Silicones) and silsesquioxane crosspolymers (such as the "KSP" series sold by Shin-Etsu Silicones), and mixtures thereof.

Active Agents

Active agents suitable for use herein include those capable of providing care and/or treatment to the skin, lips, hair, and/or nails. Examples of such ingredients include, but are not limited to, UVA/UVB sunscreen agents, lightening/bleaching agents, tanning/coloring agents, vitamins, antiperspirant/deodorant agents, anti-acne agents, anti-aging agents, anti-wrinkle agents, anti-inflammatory agents, antioxidants, antibacterial agents, antifungal agents, and mixtures thereof.

There are a number of other ingredients approved for use in the cosmetic art that may be used in compositions of the present invention. Such ingredients are those approved for use in cosmetics and can be found listed in reference books such as the *CTFA International Cosmetic Ingredient Handbook*, Tenth Edition, The Cosmetic, Toiletry, and Fragrance Association, Inc. 2004. Said materials may be used provided their inclusion does not significantly disrupt the composition once it has been applied wherein a film has been formed on the skin, hair, and/or nails. Said ingredients include preservatives, fragrances, flavor oils, and the like. Hypoallergenic compositions can be made into the present invention where said compositions do not contain fragrances, flavor oils, lanolin, sunscreens, particularly PABA, or other sensitizers and irritants.

Composition Rheology

In preferred embodiments of the present invention, final compositions may have rheological properties in a specified range to achieve the most desirable set of properties with respect to application/spreading, durability along-wear, and/or stability.

Compositions of the present invention may have a viscosity (25° C.) at low shear rates (i.e., in the range $1\ s^{-1}$-$10\ s^{-1}$) from at least about 4 Pa-s (4,000 cP), preferably from at least about 6 Pa-s (6,000 cP), more preferably from at least about 8 Pa-s (8,000 cP), even more preferably from at least about 10 Pa-s (10,000 cP), most preferably from at least about 12 Pa-s (12,000 cP) and no more than about 2,000 Pa-s (2,000,000 cP), preferably no more than about 1,000 Pa-s (1,000,000 cP), more preferably no more than about 600 Pa-s (600,000 cP), even more preferably no more than about 400 Pa-s (400,000 cP), most preferably no more than about 200 Pa-s (200,000 cP).

Compositions of the present invention may have a viscosity (25° C.) at high shear rates (i.e., in the range $400\ s^{-1}$-$500\ s^{-1}$) from at least about 0.5 Pa-s (500 cP), preferably from at least about 1 Pa-s (1,000 cP), more preferably from at least about 1.5 Pa-s (1,500 cP) and no more than about 15 Pa-s (15,000 cP), preferably no more than about 10 Pa-s (10,000 cP), more preferably no more than about 7 Pa-s (7,000 cP), most preferably no more than about 5 Pa-s (5,000 cP).

Compositions of the present invention may have an Elastic Modulus (G') (25° C.) in the Linear Viscoelastic Region (LVR) at a fixed oscillation frequency of 1 Hz from at least about 100 Pa, preferably from at least about 200 Pa, more preferably from at least about 400 Pa, even more preferably from at least about 600 Pa and no more than about $500 \times 10^3$ Pa, preferably no more than about $400 \times 10^3$ Pa, more preferably no more than about $300 \times 10^3$ Pa, even more preferably no more than about $200 \times 10^3$ Pa.

Compositions of the present invention may have a Viscous Modulus (G") (25° C.) in the Linear Viscoelastic Region (LVR) at a fixed oscillation frequency of 1 Hz from at least about 30 Pa, preferably from at least about 100 Pa, more preferably from at least about 150 Pa, even more preferably from at least about 200 Pa and no more than about $200 \times 10^3$ Pa, preferably no more than about $150 \times 10^3$ Pa, more preferably no more than about $100 \times 10^3$ Pa, even more preferably no more than about $80 \times 10^3$ Pa.

The ratio of G"/G' (or tan δ) in the LVR at a fixed oscillation frequency of 1 Hz for compositions of the present invention may be from at least about 0.1, preferably from at least about 0.2, more preferably from at least about 0.25 and no more than about 1.0, preferably no more than about 0.9, more preferably no more than about 0.8.

As stated herein, the combination of viscoelastic structuring and adhesive film-forming properties when combined or dispersed within the first phase aids in forming a long-wearing cosmetic composition that is able to resist migration from the intended application area and withstands physical and chemical insults (such as rubbing, washing, drinking, and eating) that would typically result in removal of an applied film from the skin, hair, or nails.

Method of Use/Application

Long-wearing and glossy cosmetic compositions of the present invention are achieved when the first structured and adhesive film-forming fatty phase is combined with the second fatty phase.

In one acceptable embodiment, first structured and adhesive film-forming fatty phase and second fatty phase are combined and homogeneously blended into a single composite composition that remains a stable composite composition over time. By "homogeneous" it is meant that it is macroscopically uniform in structure and composition. By "stable" it is meant that it is capable of remaining homogeneous and functional with no separation (or only very minor separation) occurring over a period of several months to several years when stored at room temperature (25° C.) and atmospheric pressure (760 mm Hg). In this particular embodiment, the composite composition may take on a variety of different product forms in addition to being liquid (such as creams, pastes, and solids). When heated sufficiently to be liquefied, lipidic components that are pasty and/or solid at room temperature can be homogeneously blended at significant levels to produce paste-like and/or solid product forms upon subsequent cooling of the composition. In this particular embodiment, the single composite composition can be manufactured as such, and used by consumers repeatedly over time without any further blending or maintenance of product uniformity. Any means of product application to skin, hair, and/or nails can be utilized that is suitable for delivering the chosen product form. Such means include, but are not limited to, sticks, pomades, brushes, bristled wands, doe foot wands, sponges, pads, squeeze tubes, liquid dispensing pumps, and liquid dispensing pens.

Test Methods

The following sections provide specifics of the instrumentation and test methodologies used to determine the relevant features described for preferred embodiments of the present invention.

Unless otherwise stated, all rheological testing is performed utilizing a ThermoHaake RS300 model rheometer running Rheowin Pro Job Manager software (Version 2.93), in combination with a ThermoHaake DC30 Thermocontroller and K20 Circulating Water Bath for temperature control.

It is also important to note that in the course of evaluating structured aqueous polymeric adhesive phases of the present invention, it was observed that very low Relative Humidity (i.e., less than 40%, especially less than 30%) would often cause rapid evaporation and dry out of material around the plate edge during the period of testing. This led to increasing edge effects and apparent changes in rheological properties of the material during testing if steps were not taken to establish adequate Relative Humidity (i.e., 35% to 60%, preferably 40% to 60%) around the instrumentation.

Viscosity Curve (Steady Shear Rheometry-Controlled Rate Rotation)

For the structured aqueous polymeric adhesive phase, viscosity response as a function of changing shear rate is determined by the following method and conditions:

1. A "PP20Ti" Sensor (Titanium Parallel Plate, 20 mm diameter) is used in combination with a 20 mm or larger base Measuring Plate. A 35 mm base Measuring Plate is typically used to maintain the most consistent contact of product in the gap between plates throughout the measurement process.
2. With the temperature controller programmed to maintain a constant 25° C.±0.2° C., the plates are moved into contact to establish the "zero position" gap, and then moved apart to allow loading of a sample.
3. Using a small stainless steel spatula, sample is loaded onto the base Measuring Plate, and the base Measuring Plate is raised to achieve a 0.100 mm gap with the PP20Ti Sensor.
4. With the gap set, the straight edge of a spatula is used to carefully remove excess material away from the edge of the Sensor plate without disturbing the Sensor position (straight edge spatula is placed in contact with Sensor edge and base Measuring Plate, and slowly drawn radially outward in successive strokes around the Sensor to remove the excess material from around the edge).
5. Having removed the excess material, a linear (or logarithmic) controlled rate sweep is performed from $0\ s^{-1}$ to $500s^{-1}$ in a 60 second period collecting a minimum of 90 data points, followed immediately with a linear (or logarithmic) controlled rate sweep from $500s^{-1}$ back to $0\ s^{-1}$ in a 60 second period collecting a minimum of 90 data points. Resulting data for viscosity response as a function of shear rate are viewed graphically on either a linear-linear or log-log scaling basis.
6. Having completed the sample measurement, the plates are moved apart to be thoroughly cleaned of material (using an isopropyl alcohol/water mixture) and dried. The process is repeated again with additional material as needed in order to obtain an accurate, reproducible set of results for each sample (typically at least 2 to 3 times).

For the total composition, viscosity response as a function of changing shear rate is determined by the following method and conditions:

1. A "PP20Ti" Sensor (Titanium Parallel Plate, 20 mm diameter) is used in combination with a 20 mm or larger base Measuring Plate. A 35 mm base Measuring Plate is typically used to maintain the most consistent contact of product in the gap between plates throughout the measurement process.
2. With the temperature controller programmed to maintain a constant 25° C.±0.2° C., the plates are moved into contact to establish the "zero position" gap, and then moved apart to allow loading of a sample.
3. Using a small stainless steel spatula, sample is loaded onto the base Measuring Plate, and the base Measuring Plate is raised to achieve a 0.100 mm gap with the PP20Ti Sensor.
4. With the gap set, the straight edge of a spatula is used to carefully remove excess material away from the edge of the Sensor plate without disturbing the Sensor position (straight edge spatula is placed in contact with Sensor edge and base Measuring Plate, and slowly drawn radially outward in successive strokes around the Sensor to remove the excess material from around the edge).
5. Having removed the excess material, a linear (or logarithmic) controlled rate sweep is performed from $0\ s^{-1}$ to $500\ s^{-1}$ in a 120 second period collecting a minimum of 90 data points, followed immediately with a linear (or logarithmic) controlled rate sweep from $500s^{-1}$ back to $0\ s^{-1}$ in a 120 second period collecting a minimum of 90 data points. Resulting data for viscosity response as a function of shear rate are viewed graphically on either a linear-linear or log-log scaling basis.
6. Having completed the sample measurement, the plates are moved apart to be thoroughly cleaned of material (using an isopropyl alcohol/water mixture) and dried. The process is repeated again with additional material as needed in order to obtain an accurate, reproducible set of results for each sample (typically at least 2 to 3 times).

Dynamic Oscillatory Stress Sweep

For the structured aqueous polymeric adhesive phase, Elastic Modulus (G') and Viscous Modulus (G") responses as a function of increasing stress at a fixed frequency are determined by increasing shear stress in an oscillatory mode according to the following method and conditions:

1. A "PP20Ti" Sensor (Titanium Parallel Plate, 20 mm diameter) is used in combination with a 20 mm or larger base Measuring Plate. In this case, a 20 mm base Measuring plate is typically used since it had been found to maintain a consistent contact of product in the gap between plates throughout the measurement process.
2. With the temperature controller programmed to maintain a constant 25° C.±0.2° C., the plates are moved into contact to establish the "zero position" gap, and then moved apart to allow loading of a sample.
3. Using a small stainless steel spatula, sample is loaded onto the base Measuring Plate, and the base Measuring Plate is raised to achieve a 0.100 mm gap with the PP20Ti Sensor.
4. With the gap set, the straight edge of a spatula is used to carefully remove excess material away from the edge of the Sensor plate without disturbing the Sensor position (straight edge spatula is placed in contact with base Measuring Plate, and slowly drawn away in successive strokes around the Sensor to remove the excess material from around the edge).

5. Having removed the excess material, a controlled stress sweep is performed at an oscillation frequency of 1 Hz starting from either 0.10 Pa or 1.00 Pa (depending on the degree of viscosity inherent to a given sample) using "optimized" repetitions to collect a minimum of 20 data points in logarithmic steps up to 1000 Pa. Resulting data for G', G" responses as a function of applied stress are viewed graphically on a log-log scaling basis.

6. Having completed the sample measurement, the plates are moved apart to be thoroughly cleaned of material (using an isopropyl alcohol/water mixture) and dried. The process is repeated again with additional material as needed in order to obtain an accurate, reproducible set of results for each sample (typically at least 2 to 3 times).

For the total composition, Elastic Modulus (G') and Viscous Modulus (G") responses as a function of increasing stress at a fixed frequency are determined by increasing shear stress in an oscillatory mode according to the following method and conditions:

1. A "PP20Ti" Sensor (Titanium Parallel Plate, 20 mm diameter) is used in combination with a 20 mm or larger base Measuring Plate. In this case, a 20 mm base Measuring Plate is typically used since it had been found to maintain a consistent contact of product in the gap between plates throughout the measurement process.

2. With the temperature controller programmed to maintain a constant 25° C.±0.2° C., the plates are moved into contact to establish the "zero position" gap, and then moved apart to allow loading of a sample.

3. Using a small stainless steel spatula, sample is loaded onto the base Measuring Plate, and the base Measuring Plate is raised to achieve a 0.100 mm gap with the PP20Ti Sensor.

4. With the gap set, the straight edge of a spatula is used to carefully remove excess material away from the edge of the Sensor plate without disturbing the Sensor position (straight edge spatula is placed in contact with base Measuring Plate, and slowly drawn away in successive strokes around the Sensor to remove the excess material from around the edge).

5. Having removed the excess material, a controlled stress sweep is performed at an oscillation frequency of 1 Hz starting from either 0.10 Pa or 1.00 Pa (depending on the degree of viscosity inherent to a given sample) using "optimized" repetitions to collect a minimum of 30 data points in logarithmic steps up to 2000 Pa. Resulting data for G', G" responses as a function of applied stress are viewed graphically on a log-log scaling basis.

6. Having completed the sample measurement, the plates are moved apart to be thoroughly cleaned of material (using an isopropyl alcohol/water mixture) and dried. The process is repeated again with additional material as needed in order to obtain an accurate, reproducible set of results for each sample (typically at least 2 to 3 times).

EXAMPLES

The following examples illustrate the claimed cosmetic compositions of the present invention but are not intended to be limiting thereof:

Example 1

Long-Wearing Lipcolor or Lipgloss

| Ingredient | w/w % |
| --- | --- |
| Part A | |
| Isopropyl Isostearate | 13.00 |
| Octyl Hydroxystearate | 8.50 |
| Castor Oil | 5.00 |
| C30-C38 Olefin/Isopropyl Maleate/MA Copolymer[1] | 2.00 |
| PVP/Eicosene Copolymer[2] | 2.00 |
| Candelilla Wax | 3.00 |
| Carnauba Wax | 2.00 |
| Ozokerite | 4.00 |
| Paraffin | 2.40 |
| Acetylated Lanolin | 6.00 |
| Cetyl Lactate | 2.00 |
| Propylparaben | 0.10 |
| Part B | |
| Castor Oil | 17.50 |
| Coloring Agents (pigments) | 7.50 |
| Part C | |
| Dimethicone, 50 cSt | 10.00 |
| Phenyltrimethicone[3] | 15.00 |

[1]Performa V ® 1608 Polymer (New Phase Technologies, Inc.)
[2]GANEX ® V-220F (ISP Corporation)
[3]DOW CORNING ® 556 Cosmetic Grade Fluid (Dow Corning Corporation)

Example 1 is assembled according to the following procedure:

In a suitably sized vessel for Part B, the coloring agents are gradually added into the castor oil while being mixed with a conventional mixer until full wetting and/or dispersion has occurred. Further particle size reduction of the coloring agents in the castor oil is then achieved using conventional wet grinding or milling technology (e.g., three-roll mill, media mill) on this mixture.

In a separate suitably sized vessel equipped for heating and mixing, all the ingredients of Part A are combined together with the completed/milled Part B mixture. Heat the combined ingredients to about 90° C.-95° C., and mix the ingredients sufficiently while maintaining heat on the mixture to ensure all ingredients are melted completely and liquefied together. The temperature of this liquefied mixture is then reduced to about 80° C.-85° C. while continuing to mix.

The ingredients of Part C are then either combined together with one another first to be added as a mixture to the previous ingredients, or added individually to the previous ingredients. The ingredients of Part C are added in a gradual, controlled rate to the previous ingredients while maintaining sufficient heating and mixing to ensure rapid and complete dispersion of Part C ingredients throughout the composition. Following complete addition of Part C ingredients, the composition is immediately poured into a suitable room temperature (or slightly chilled) receiving container (e.g., plastic/glass jar or tube, or aluminum mold), and cooled rapidly and for a sufficient period of time so as to obtain a solid/semi-solid form.

Examples of Structured Aqueous Polymeric Adhesive Phase

The following examples are representative of a structured aqueous polymeric adhesive phase prepared by combining a structuring agent with an aqueous dispersion of adhesive film-forming polymer particles of the present invention. The structuring agent is gradually added while being mixed continuously with a conventional mixer until full dispersion and structuring of this phase has occurred:

| Ingredient | Example 2 w/w % | Example 3 w/w % | Example 4 w/w % | Example 5 w/w % |
|---|---|---|---|---|
| Aqueous Dispersion of Polyether-Polyurethane (33% Polymer in Water)[1] | 99.50 | 95.50 | 92.00 | 92.00 |
| Sodium Carboxymethylcellulose[2] | 0.50 | — | — | — |
| Allyl Methacrylates Copolymer[3] | — | 4.50 | — | — |
| Fumed Silica[4] | — | — | 8.00 | — |
| Sodium Magnesium Silicate[5] | — | — | — | 8.00 |

[1]Polyderm PE-PA (ALZO International, Inc.)
[2]Cekol 30,000 (Noviant, Inc.)
[3]POLYPORE ® E-200 (AMCOL Health & Beauty Solutions, Inc.)
[4]Silica Shells (KOBO Products, Inc.)
[5]LAPONITE ® XLG (Southern Clay Products, Inc.)

Example 6 and Example 7

Long-Wearing Lipcolor or Lipgloss

Long-wearing lipcolor or lipgloss is prepared using a structured aqueous polymeric adhesive phase as the film-forming agent within the present invention as follows:

| Ingredient | Example 6 w/w % | Example 7 w/w % |
|---|---|---|
| Part A | | |
| Structured Aqueous Polymeric Adhesive Phase of Example 2 | 15.00 | 13.00 |
| Part B | | |
| Castor Oil | 17.50 | 20.50 |
| Coloring Agents (pigments) | 7.50 | 7.50 |
| Part C | | |
| Ozokerite | 4.50 | 2.00 |
| Paraffin | 2.50 | 1.25 |
| Polyethylene[1] | 2.00 | — |
| C30-C38 Olefin/Isopropyl Maleate/MA Copolymer | 2.00 | — |
| Candelilla Wax | — | 1.25 |
| Methylparaben | 0.15 | 0.15 |
| Propylparaben | 0.15 | 0.15 |
| Phenyl Trimethicone and Dimethicone/Phenyl Vinyl Dimethicone Crosspolymer[2] | 15.00 | 15.00 |
| Dimethicone, 50 cSt | 5.00 | 5.00 |
| Trimethyl Pentaphenyl Trisiloxane[3] | 28.70 | 34.20 |

[1]PERFORMALENE ® 400 Polyethylene (New Phase Technologies, a division of Bake Petrolite Corporation)
[2]KSG-18 (Shin-Etsu Silicones of America, Inc.)
[3]DOW CORNING ® PH-1555 HRI Cosmetic Fluid (Dow Corning Corporation)

In a suitably sized vessel, the structured aqueous polymeric adhesive phase of Example 2 is prepared. Starting with the aqueous dispersion of polyether-polyurethane in the vessel, the sodium carboxymethylcellulose is gradually added while being mixed continuously with a conventional mixer until full dispersion and structuring of this phase has occurred.

In a suitably sized vessel for Part B, the coloring agents are gradually added into the castor oil while being mixed with a conventional mixer until full wetting and/or dispersion has occurred. Further particle size reduction of the coloring agents in the castor oil is then achieved using conventional wet grinding or milling technology (e.g., three-roll mill, media mill) on this mixture.

In a separate suitably sized vessel equipped for heating and mixing, all of the ingredients of Part C are combined together. Heat the combined Part C ingredients to about 85° C.-95° C., and mix the ingredients sufficiently while maintaining heat on the mixture to ensure all ingredients are melted completely and liquefied together. The temperature of this liquefied mixture is then reduced to about 80° C.-85° C. while continuing to mix.

Part A and Part B are combined together with one another and mixed thoroughly to be added as a mixture to Part C. The combined mixture of Part A and Part B ingredients is added in a gradual, controlled rate to Part C while maintaining sufficient heating and mixing to ensure rapid and complete dispersion of ingredients throughout the composition. Following complete addition and mixing of ingredients, the composition is immediately poured into a suitable room temperature (or slightly chilled) receiving container (e.g., plastic/glass jar or tube, or aluminum mold), and cooled rapidly and for a sufficient period of time so as to obtain a solid/semi-solid form.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the term in a document incorporated herein by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition comprising:
(A) from about 30% to about 95% by weight of the composition of a first structured and adhesive film-forming fatty phase (A) comprising:
   i) from about 10% to about 98.5% by weight of the first structured of one or more lipidic components that are mutually compatible with one another when liquefied, wherein the lipidic component comprises less than about 50% of a volatile liquid;
   ii) a structured aqueous polymeric adhesive phase comprising at least one aqueous dispersion of adhesive film-forming polymer particles which are free of volatile organic compounds and at least one structuring agent in an amount effective to viscoelastically thicken, but not solidify, the structured aqueous polymeric adhesive phase, and wherein the adhesive film forming polymer is present in an amount of about 1% to 60% by weight of the first structured and adhesive film-forming fatty phase (A); and
   iii) from about 0.50% to about 60% by weight of the first structured and adhesive film-forming fatty phase (A) of at least one lipophilic structuring agent in an amount effective to retain a second fatty phase entrapped in said cosmetic composition prior to application on mammalian keratinous tissue; and
(B) from about 5% to about 70% by weight of the composition of a second fatty phase (B) comprising at least one non-volatile lipidic component, the non-volatile lipidic component being at least 10% by weight of the lipidic component of the second fatty phase (B),
said second fatty phase (B) being incompatible with said first structured and adhesive film-forming fatty phase (A) and said second fatty phase (B) being entrapped in said composition where upon application of said composition to mammalian keratinous tissue, said second fatty phase (B) readily separates from said composition to form a barrier layer over said first structured and adhesive film-forming fatty phase (A) said composition being substantially free of surfactants such that separation of said second fatty phase (B) from said composition is not prevented following application of said composition; and wherein the composition is a single composite composition that remains stable over time.

2. The cosmetic composition of claim 1 wherein the structured aqueous polymeric adhesive phase has a viscosity from about 2 Pa-s to about 60 Pa-s at low shear rates and from about 0.5 Pa-s to about 5 Pa-s at high shear rates.

3. The cosmetic composition of claim 1 wherein the structured aqueous polymeric adhesive phase has an Elastic Modulus (G') from about 5 Pa to about 100 Pa, and a Viscous Modulus (G") from about 15 Pa to about 300 Pa in the Linear Viscoelastic Region at 25° C. and 1 Hz fixed oscillation frequency.

4. The cosmetic composition of claim 3 wherein the structured aqueous polymeric adhesive phase has a ratio of G"/G' (tan δ) from about 1.5 to about 5.5 in the Linear Viscoelastic Region at 25° C. and 1 Hz fixed oscillation frequency.

5. The cosmetic composition of claim 1 wherein the second fatty phase (B) has a viscosity of from about 1 cSt to about 5,000 cSt.

6. The cosmetic composition of claim 1 wherein the nonvolatile lipidic component of the second fatty phase (B) has a refractive index at 20° C. of at least about 1.450.

7. The cosmetic composition of claim 1 wherein the surface tension of the second fatty phase (B) is less than about 35 dynes/cm.

8. The cosmetic composition of claim 1 further comprising one or more of coloring agents, fillers/bulking agents, active agents, preservatives, fragrances, flavor oils, and mixtures thereof.

* * * * *